US010835716B2

(12) United States Patent
Kim et al.

(10) Patent No.: US 10,835,716 B2
(45) Date of Patent: Nov. 17, 2020

(54) STEERABLE MEDICAL DEVICE AND THE PREPARING METHOD THEREOF

(71) Applicants: XCATH, INC., Houston, TX (US); THE BOARD OF REGENTS OF THE UNIVERSITY OF TEXAS SYSTEM, Austin, TX (US)

(72) Inventors: Daniel H. Kim, Houston, TX (US); Dong Suk Shin, Houston, TX (US); Viljar Palmre, Pearland, TX (US); Younghee Shim, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/478,435

(22) PCT Filed: Jul. 27, 2018

(86) PCT No.: PCT/US2018/044059
§ 371 (c)(1),
(2) Date: Jul. 16, 2019

(87) PCT Pub. No.: WO2019/027826
PCT Pub. Date: Feb. 7, 2019

(65) Prior Publication Data
US 2020/0139084 A1    May 7, 2020

Related U.S. Application Data

(60) Provisional application No. 62/539,346, filed on Jul. 31, 2017.

(51) Int. Cl.
*A61M 25/01*    (2006.01)
*A61L 29/04*    (2006.01)
(Continued)

(52) U.S. Cl.
CPC ....... *A61M 25/0158* (2013.01); *A61L 29/041* (2013.01); *A61L 29/14* (2013.01);
(Continued)

(58) Field of Classification Search
CPC ........ A61M 25/0158; A61M 25/09041; A61M 25/0113; A61M 2025/0058;
(Continued)

(56) References Cited

U.S. PATENT DOCUMENTS

| 5,415,633 A | 5/1995 | Lazarus |
| 6,117,296 A | 9/2000 | Thomson |
| 2007/0250036 A1 | 10/2007 | Volk et al. |
| 2008/0146967 A1 | 6/2008 | Richardson et al. |

(Continued)

FOREIGN PATENT DOCUMENTS

| CN | 102551672 A | 7/2012 |
| JM | H0810336 A | 1/1996 |

(Continued)

OTHER PUBLICATIONS

Australian Application No. 2018311844, Examination Report No. 1 dated Dec. 6, 2019, 4 pages.
(Continued)

*Primary Examiner* — Rebecca E Eisenberg
*Assistant Examiner* — Anh Bui
(74) *Attorney, Agent, or Firm* — Patterson + Sheridan, LLP

(57) ABSTRACT

A medical device includes at least one ionic electroactive polymer actuator, the actuator including at least one polymer electrolyte member defining at least a surface and a plurality of electrodes disposed about the surface of the at least one polymer electrolyte member, an elongate, flexible portion defining a proximal end and a distal end secured adjacent to the ionic electroactive polymer actuator and the elongate, flexible portion further comprising a core and a sleeve surrounding the core and a plurality of electrically-conduc- (Continued)

tive wires, each having a proximal end and a distal end coupled to at least one of the plurality of electrodes, wherein the at least one polymer electrolyte member deforms asymmetrically in response to the application of an electrical potential supplied through at least one of the plurality of electrically-conductive wires to at least one of the plurality of electrodes.

23 Claims, 19 Drawing Sheets

(51) Int. Cl.
  *A61L 29/14* (2006.01)
  *A61B 1/005* (2006.01)
  *A61M 25/09* (2006.01)

(52) U.S. Cl.
  CPC .. *A61B 1/0057* (2013.01); *A61M 2025/09133* (2013.01); *A61M 2205/0238* (2013.01); *A61M 2205/0283* (2013.01)

(58) Field of Classification Search
  CPC ......... A61M 2025/09133; A61M 2025/09175; A61M 2205/0283
  See application file for complete search history.

(56) References Cited

U.S. PATENT DOCUMENTS

| 2013/0123692 A1 | 5/2013 | Zhang et al. |
| 2015/0032027 A1 | 1/2015 | Lupton |

FOREIGN PATENT DOCUMENTS

| JP | 2007209554 A | 8/2007 |
| JP | 2009-535092 A | 10/2009 |
| WO | 2007126452 A2 | 11/2007 |
| WO | 2015-158757 A1 | 10/2015 |

OTHER PUBLICATIONS

Canadian Patent Application No. 3,039,269, Office Action dated Dec. 16, 2019, 3 pages.
PCT International Search Report and Written Opinion for PCT/US2018/044059, dated Jan. 24, 2019.
Taiwan Application No. 107126073, Office Action/Search Report dated Jul. 5, 2019 w/translation, 11 pages.
Tina Shoa et al., Conducting Polymer Based Active Catheter for Minimally Invasive Interventions Inside Arteries, 2008 30th Annual International Conference of hte IEEE Engineering in Medicine and Biology Society, 4 pages.
Korean Patent Application No. 10-2019-7010800, Notice of Grounds for Rejection dated Dec. 11, 2019, 6 pages.
Japanese Patent Application No. 2019-520807, Office Action dated Jul. 7, 2020 w/translation, 5 pages.

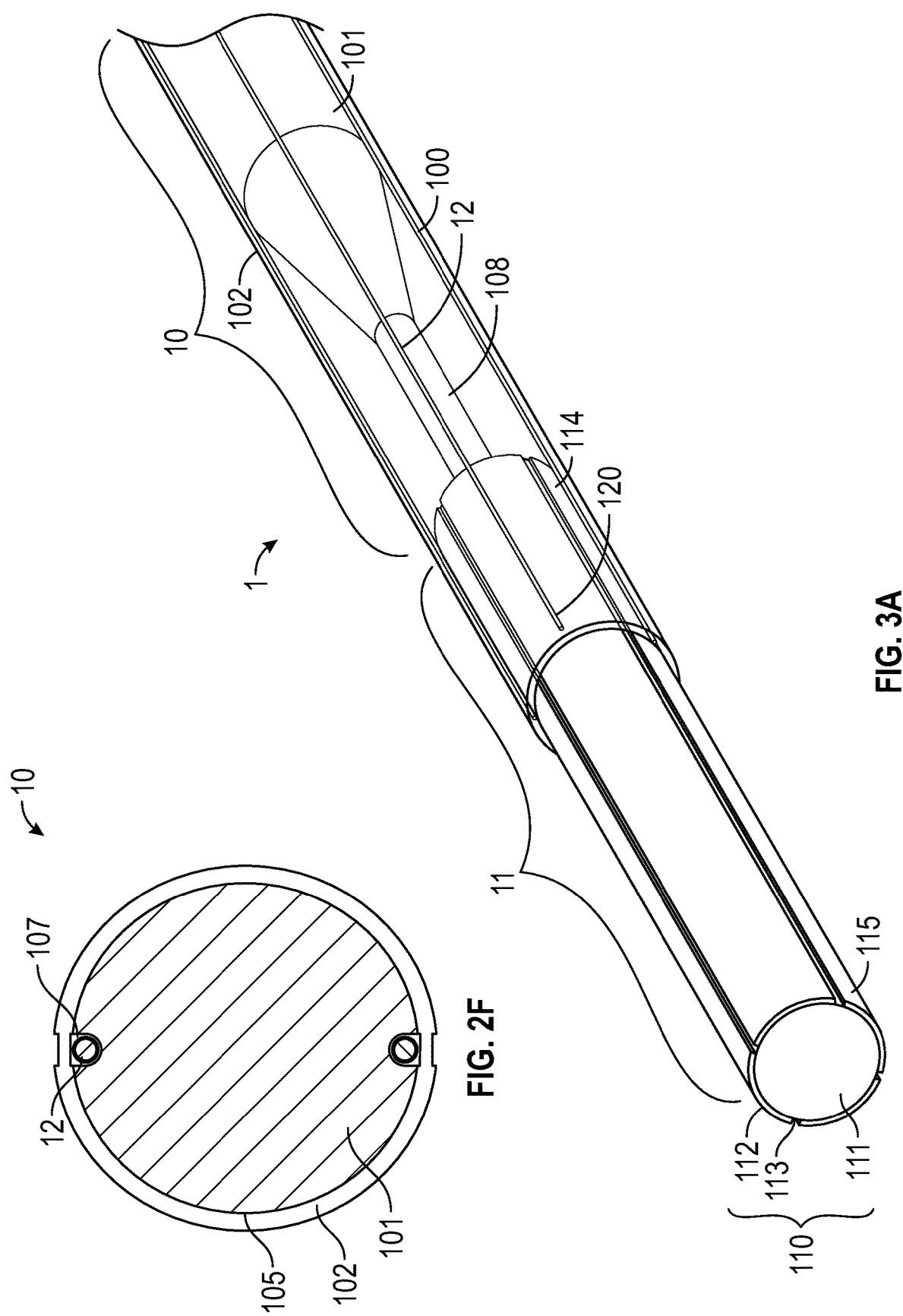

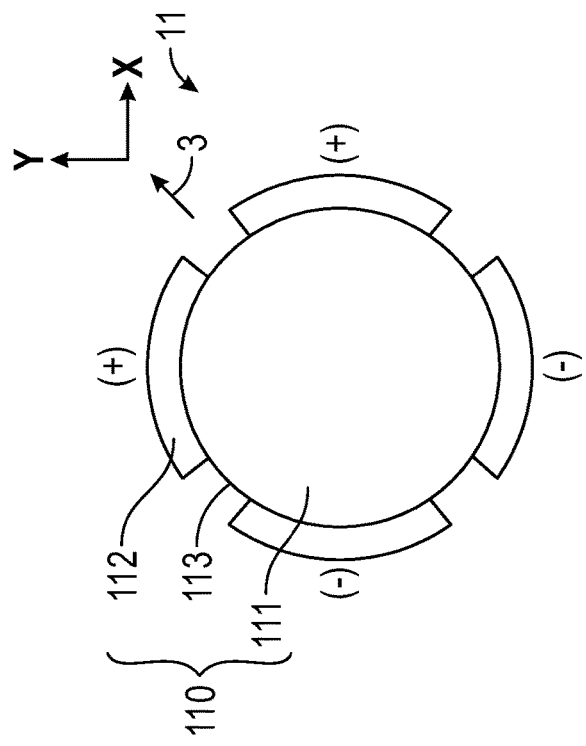
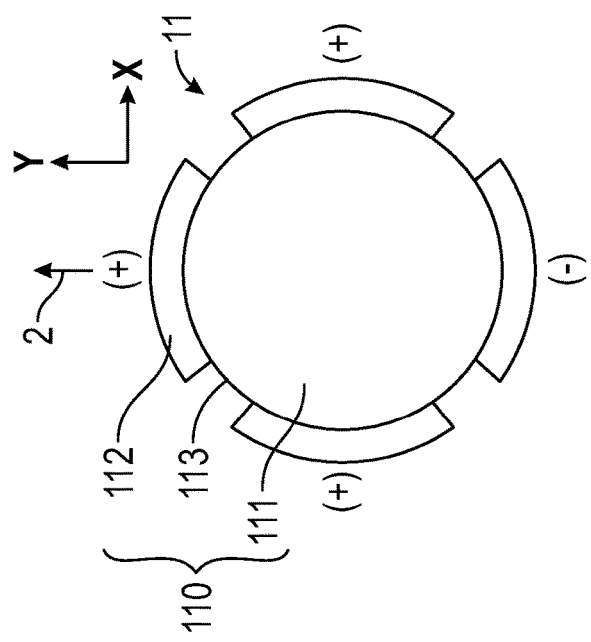
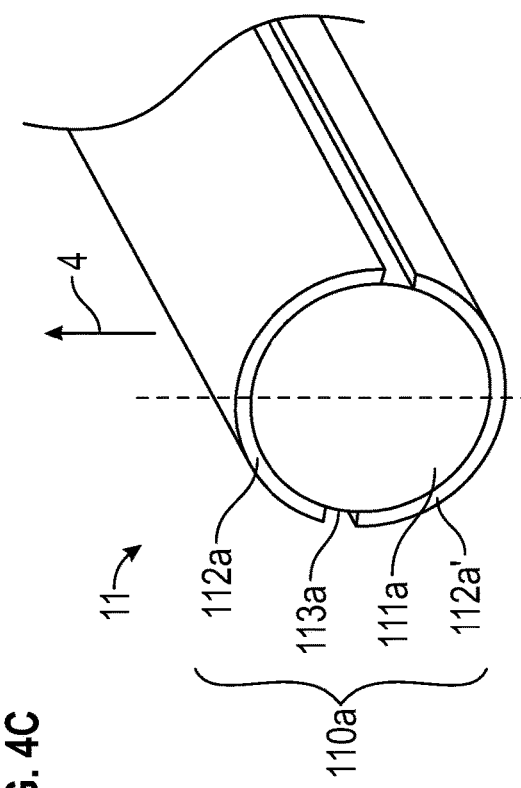

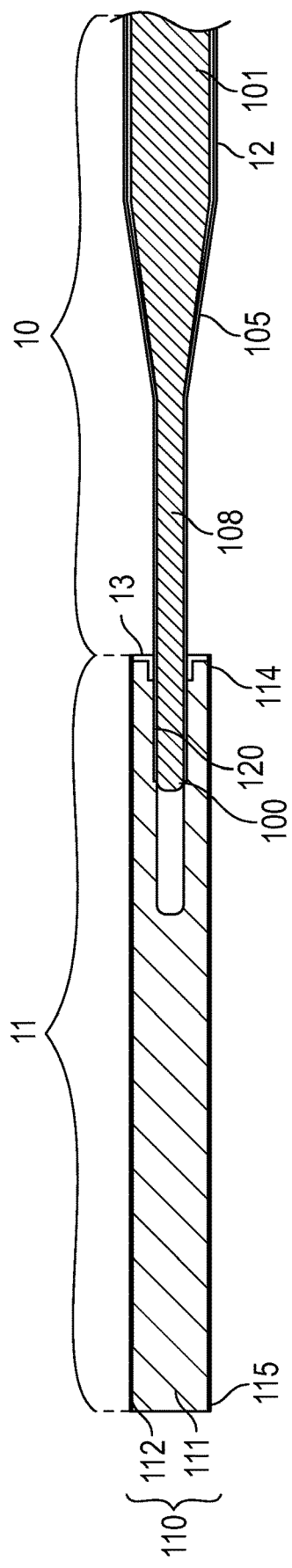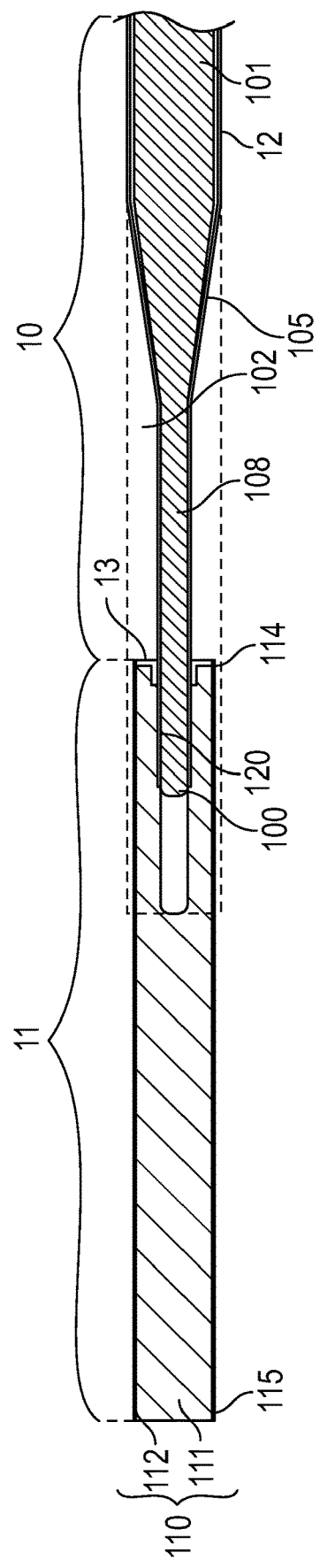
FIG. 7A
FIG. 7B

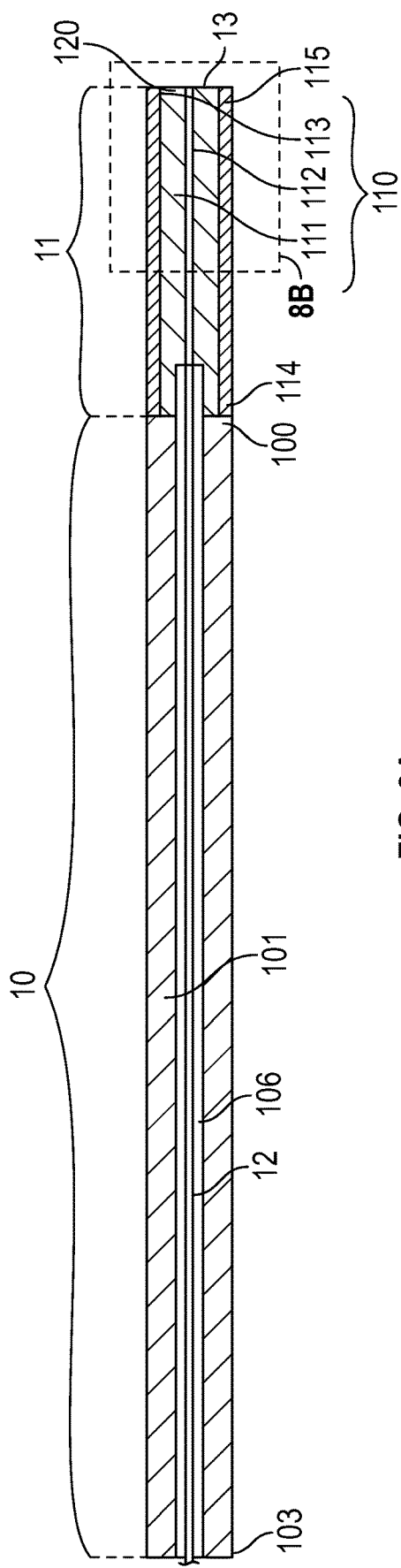
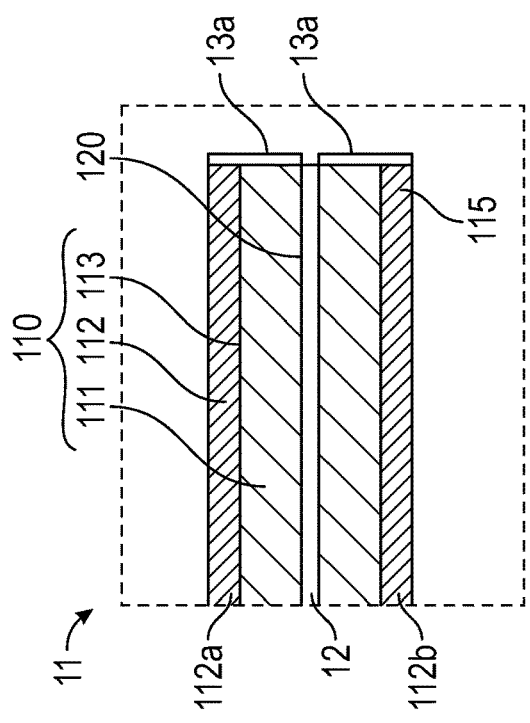
FIG. 8A
FIG. 8B

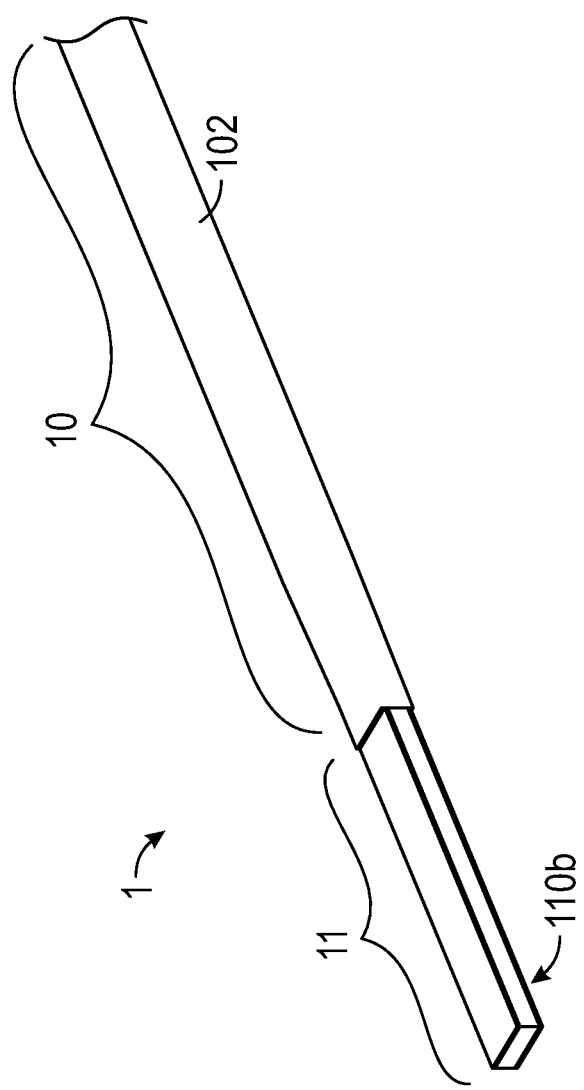
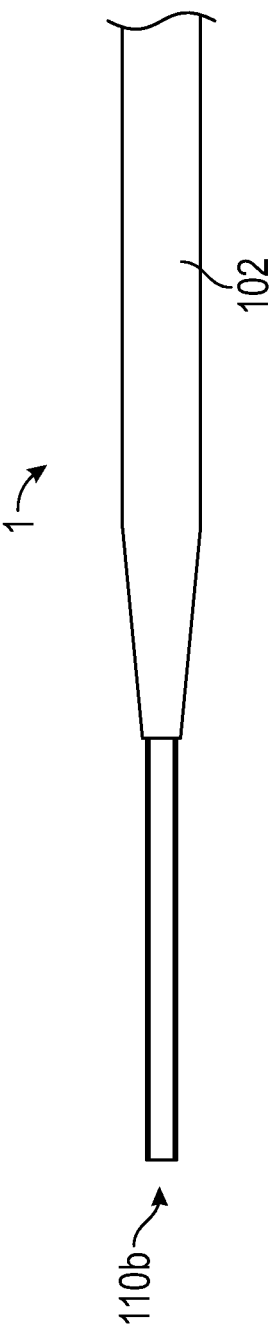
FIG. 11A
FIG. 11B

STEERABLE MEDICAL DEVICE AND THE PREPARING METHOD THEREOF

CROSS-REFERENCE TO RELATED APPLICATION

The present Application for Patent is a national stage application under 35 U.S.C. 371 of PCT/US2018/044059, filed Jul. 27, 2018, which claims priority to U.S. Provisional Application No. 62/539,346, filed Jul. 31, 2017, which are both assigned to the assignee of the present application and expressly incorporated by reference in their entireties.

BACKGROUND OF THE INVENTION

Field of the Invention

The invention relates to a steerable intraluminal medical device and, more particularly, to a flexible, narrow medical device (such as a guidewire) introduced into and controllably moved through lumens of a body. In an embodiment, the medical device includes an electrically-actuatable bendable portion at a distal, leading, end thereof which can be selectively manipulated for steering the medical device to a targeted anatomical location within a body.

Discussion of the Related Art

Intraluminal medical devices have various structures depending on the location of their intended deployment within the body and the intended method of treatment using the devices. Intraluminal devices generally include a very slender, i.e., very small in cross section, and flexible, tube that can be inserted into and guided through a body lumen such as an artery or a vein, or a bodily passageway such as a throat, a urethra, a bodily orifice or some other anatomical passage. Examples of such medical devices include syringes, endoscopes, catheters, guide wires and other surgical instruments.

For example, guide wires are commonly used to navigate vessels to reach a target lumen, bodily passageway, bodily orifice or anatomical passage. Once the guide wire reaches the target location within a body, a catheter, stent or other medical device may be guided to the target location by movement over or along the guide wire.

Conventional guide wires improve access to treatment locations within the patient's body but offer poor directional control because of their high flexibility. The flexibility is required to allow the guidewire to move through tortuous pathways in a lumen or passage. However, this same flexibility results in the aforementioned poor control of the direction or path the distal end of the guidewire will take when it is pushed at its proximal end. Thus, there is a need for improved guide wires having better steering control.

SUMMARY OF THE INVENTION

Embodiments of the steerable intraluminal medical device provide improved steering control and intra-body positioning of an actuation part (e.g., a guidewire) of a medical device wherein the actuation part is adapted to be introduced into a lumen or into a bodily passage or lumen of a body and manipulated while the actuation part is being pushed inwardly of the body for movement into and through the lumen or bodily passage to dispose a distal end of the actuation part of the medical device at a desired anatomical location within the body. Embodiments of the medical device provide more precise control of movement and positioning of one or more manipulatable microsurgical components disposed at the distal, leading, end, of the actuation part of the medical device for performing a surgical procedure or other medical operation at the desired location within the body.

One embodiment of a medical device may have an actuation part in a guidewire form to be moved into or through a lumen or a bodily passage. The medical device comprises a slender, elongate and flexible portion having a distal end and a proximal end, and an ionic electroactive polymer actuator comprising a polymer electrolyte member disposed adjacent to the distal end of the elongate and flexible portion. One embodiment of the elongate and flexible portion may further comprise a core extending from the proximal end to the distal end, and a sleeve surrounding the core. The ionic electroactive polymer actuator, as will be discussed in greater detail below, is an actuator comprising a polymer electrolyte member in which cations are free to migrate in response to an electrical field imposed thereon. The electrical field is provided through energization of a plurality of distributed electrodes disposed and spaced about a circumference of the polymer electrolyte member. The plurality of distributed electrodes are one of embedded in, deposited on, and secured against at least a portion of at least a surface of the polymer electrolyte member. Each of the plurality of electrodes may be connected to a source of electrical potential through one or more electrically-conductive wires such as, for example, a metal wire extending over the core of the elongate, flexible portion and having a proximal end coupled to the source of electrical potential and a distal end coupled to the electrode. Selective electrical energization of one or more, but not all, of the plurality of electrodes causes the polymer electrolyte member to deform asymmetrically as a result of contracting along a side or portion of the polymer electrolyte member and/or swelling along a side or portion of the polymer electrolyte member.

In some embodiments, the outer surface of the core can be linearly tapered, tapered in a curvilinear fashion, or tapered in a step-wise fashion from the distal end of the elongate, flexible, portion to form a reduced thickness, reduced width, or reduced diameter end. The angle of any such tapered end can vary, depending upon the desired flexibility characteristics. The length of the tapered end may be selected to obtain a more gradual (longer taper length) or less gradual (shorter taper length) transition in stiffness. In some embodiments, the tapered end may include a tapering outer diameter distally so that a portion of the core is reduced in cross section and thus can be embedded into the polymer electrolyte member. In some embodiments, the core has a solid cross-section. But in some alternative embodiments, the core can have a hollow cross-section. For example, in some embodiments, an inner lumen is provided and formed longitudinally within the core from the proximal end to the distal end thereof. In other embodiments, the core may comprise a metallic material and couple to at least one of the plurality of electrodes to serve as an additional electrically-conductive conduit.

In some embodiments, the sleeve may extend from the distal end of the elongate, flexible portion to surround at least a portion of the ionic electroactive polymer actuator. For example, the sleeve may surround one of the electrodes, the polymer electrolyte member, or a combination thereof.

The electrically-conductive wires are interconnected with the elongate and flexible portion via various means, techniques and/or structures. For example, but not by way of limitation, in one embodiment, each of the electrically-conductive wires is disposed linearly or parallelly along an exterior surface of the core, and they are spaced thereon from each other circumferentially. In an exemplary embodiment, a plurality of grooves are formed linearly, and spaced from each other circumferentially, inwardly of the exterior surface of the core, each groove receiving one of the electrically-conductive wires therein, respectively. In other embodiments, each of the plurality of electrically-conductive wires is helically or interweavingly wrapped around the core. Alternatively, in some embodiments, the electrically-conductive wires may be secured between the sleeve and the core and further be secured to at least a portion of the ionic electroactive polymer actuator. In other embodiments, the electrically-conductive wires may pass through the core, e.g. being secured or embedded through the core when the core has a solid cross-section. Alternatively, where the core has a hollow cross-section, the electrically-conductive wires may pass through the inner lumen defined within the core as described above.

To insulate the electrically-conductive wires from the elongate and flexible portion and the ionic electroactive polymer actuator except where contact therewith is desired, each of the plurality of electrically-conductive wires may further comprise an insulation coating thereon. The material of the insulation coating may comprise for example, but is not limited to, ceramic, PTFE, nylon, polyimide, polyester or a combination thereof.

In some embodiments, the polymer electrolyte member may comprise a polymer host and an electrolyte as solvent. The polymer may comprise, but is not limited to, fluoropolymers and intrinsically conducting polymers. In an exemplary embodiment, the fluoropolymers may comprise perfluorinated ionomers, polyvinylidene difluoride (PVDF) or a co-polymer thereof (e.g. Poly(vinylidene fluoride-co-hexafluoropropylene) (PVDF-HFP), but are not limited to these polymers. In another exemplary embodiment, the intrinsically conducting polymers may comprise, but are not limited to, polyaniline (PANI), polypyrrole (Ppy), poly(3,4-ethylenedioxythiophene) (PEDOT), poly(p-phenylene sulfide) (PPS) or the combination thereof. In yet another embodiment, the electrolyte may be water or an ionic liquid. An exemplary example of the ionic liquid may include, but is not limited to, 1-ethyl-3-methylimidazolium tetrafluoroborate (EMI-BF4), 1-ethyl-3-methylimidazolium bis(trifluoromethylsulfonyl)imide (EMI-TFSI), 1-ethyl-3-methyl-imidazolium trifluoromethanesulfonate (EMITf) or the combination thereof.

In some embodiments, each of the electrodes may comprise one of platinum, gold, a carbon-based material and a combination thereof. Exemplary examples of the carbon-based material may comprise, but are not limited to, one of carbide-derived carbon, carbon nanotube(s), graphene, a composite of carbide-derived carbon and polymer electrolyte member, and a composite of carbon nanotube(s) and polymer electrolyte member.

In one embodiment of the medical device, the ionic electroactive polymer actuator may comprise a plurality of individual, and electrically isolated from one another, electrodes which are angularly distributed about at least a surface of the polymer electrolyte member. In one embodiment of the medical device, the ionic electroactive polymer actuator is included in a bendable portion at the distal end of an actuation part (e.g., a guidewire) of the medical device. For example, but not by way of limitation, the bendable portion of the medical device, in one embodiment, comprises three angularly-distributed electrodes that are separated, at their centerlines, each one from the others by about 120 degrees (2.094 radians). As another example, but not by way of limitation, the bendable portion of the medical device may comprise eight angularly-distributed electrodes that are separated, at their centerlines, by about 45 degrees (0.785 radians) from each other. It will be understood that each of the plurality of electrodes occupies a portion of the circumferential span around the surface of the polymer electrolyte member, and that the "angular separation" may therefore be stated in terms of the centerlines of the electrodes instead of in terms of the adjacent edges of the electrodes, which will be much closer to the adjacent edge of the adjacent electrodes than will be their adjacent centerlines. In some embodiments of the medical device, the electrodes are spaced in a manner to provide a substantial gap between adjacent electrodes.

In some embodiments, electrically-conductive wires are directly interconnected (e.g. are integrated and embedded) to electrodes using various conventional techniques such as soldering, crimping, stapling, pinching, welding, conductive adhesive (e.g., using conductive epoxy), and the like. Alternatively, in some embodiments, electrically-conductive wires are indirectly interconnected to the electrodes through an intervening conductive bridge. In an exemplary embodiment, the conductive bridge extends between a surface of the polymer electrolyte member and at least one of the electrodes to serve as a conductive interface to connect the electrically-conductive wires to the electrodes and allow movement therebetween without negatively impacting the electrical connection therebetween.

In some embodiments, the ionic electroactive polymer actuator can be configured in any possible configuration to provide two degrees of freedom of bending motion. For example, four electrodes are circumferentially distributed by an equal angular spacing of their centerlines about the surface of the polymer electrolyte member. In some embodiments, the ionic electroactive polymer actuator can be configured in any possible configuration to provide one degree of freedom in bending motion. In one exemplary embodiment, the polymer electrolyte member may be a right circular cylindrical, or other cross section, rod or have another rod-like shape, and two electrodes are circumferentially distributed by equal angles about the surface of the polymer electrolyte member. In another exemplary embodiment, the polymer electrolyte member may have a rectangular shape and define a top surface and a corresponding bottom surface and two electrodes are circumferentially distributed about the top surface and the bottom surface of the polymer electrolyte member symmetrically to form a sandwich structure where the electrodes sandwich the polymer electrolyte member therebetween.

BRIEF DESCRIPTION OF THE DRAWINGS

The appended illustrative drawings provide a further understanding of embodiments and are incorporated into and constitute a part of this application and, together with the written description, serve to explain the present invention. The appended drawings are briefly described as follows.

FIGS. 2A to 2F illustrate various embodiments of the elongate, flexible portion of FIG. 1A, wherein:

FIG. 2A is a cross-section view of the elongate, flexible portion according to one embodiment, illustrating two electrically-conductive wires disposed linearly, and spaced from each other circumferentially, along the exterior surface of the core.

FIG. 2B is a cross-section view of the elongate, flexible portion according to another embodiment, illustrating one electrically-conductive wire disposed linearly, and spaced from each other circumferentially, along the exterior surface of the core that further comprises a core wire.

FIG. 2C is a side view of the core of the elongate, flexible portion according to another embodiment, illustrating electrically-conductive wires helically or interweavingly wrapped around the core.

FIG. 2D is a sectional side view of the elongate, flexible portion and the bendable portion according to another embodiment, illustrating an inner lumen formed with the core along the elongate, flexible portion.

FIG. 2E is a cross-section view of the elongate, flexible portion of FIG. 2D, illustrating the electrically-conductive wires passing through the inner lumen.

FIG. 2F is a cross-section view of the elongate, flexible portion according to another embodiment, illustrating a plurality of grooves formed linearly, and spaced from each other circumferentially, along the exterior surface of the core.

FIG. 3A to 3C illustrates the elongate, flexible portion and the bendable portion of the guidewire of FIG. 1A according to various embodiments where a tapered end is provided at the distal end of the elongate, flexible portion, wherein:

FIG. 3A is an isometric view of a portion of the elongate, flexible portion and of the bendable portion according to one embodiment with a section of the polymer sleeve indicated in solid lines to better reveal details of the components therein.

FIG. 3B is a sectional side view of the elongate, flexible portion and the bendable portion of FIG. 3A according to one embodiment, illustrating a tapered end having a geometry that decreases in cross sectional area as it approaches the distal end of the elongate, flexible portion to couple with the proximal end of the ionic electroactive polymer actuator provided at the bendable portion.

FIG. 3C is a sectional side view of the elongate, flexible portion and the bendable portion of FIG. 3A according to another embodiment, illustrating a tapered end embedded into the proximal end of the polymer electrolyte member.

FIG. 4C is a cross-sectional view of the portion of the bendable portion of FIGS. 4A and 4B illustrating one embodiment where a first selected set of four electrical signals is applied to four circumferentially distributed electrodes disposed about the exterior surface of the polymer electrolyte member to provide two degrees of freedom in bending movement.

FIG. 4D is the cross-sectional view of the portion of the bendable portion of FIGS. 4A and 4B revealing another embodiment where a second selected set of four electrical signals is applied to the circumferentially distributed electrodes disposed about the polymer electrolyte member.

FIG. 5 is an isometric view of a portion of the bendable portion of the guidewire according to another embodiment illustrating a rodlike ionic electroactive polymer actuator providing one degree of freedom in bending movement.

FIG. 7A illustrates a sectional side view of the elongate, flexible portion without the polymer sleeve and the bendable portion of a guidewire according to another embodiment, illustrating a conductive bridge 13 formed at the proximal end of the ionic electroactive polymer actuator.

FIG. 7B illustrates a sectional side view of the elongate, flexible portion of FIG. 7A with the polymer sleeve.

FIG. 8A illustrates a side view of the elongate, flexible portion and the bendable portion of the guidewire having generally the same configuration, but modified, as FIG. 2D according to one embodiment.

FIG. 8B illustrates a side view of the bendable portion of FIG. 8A.

FIGS. 9A to 9C illustrate schematically the integration of the ionic electroactive polymer actuator and the tapered end provided at the distal end of the core of the elongate, flexible portion, wherein:

FIG. 9A is an exploded view showing a core and an ionic electroactive polymer actuator of a guidewire shown in FIGS. 6A and 6B according to one embodiment;

FIG. 9B is an isometric view of a core and an ionic electroactive polymer actuator of a guidewire shown in FIGS. 6A and 6B according to one embodiment; and FIG. 9C is an isometric view of FIG. 9B with a section of an ionic electroactive polymer actuator indicated in solid lines to better reveal details of the components therein.

FIGS. 10A to 10D illustrate schematically the integration of electrically-conductive wires with the electrodes of the ionic electroactive polymer actuator and the core of the elongate, flexible portion, wherein:

FIG. 10A is an isometric view of a core, an ionic electroactive polymer actuator and electrically-conductive wires of a guidewire shown in in FIGS. 6A and 6B according to one embodiment;

FIG. 10B is a side view of FIG. 10A;

FIG. 10C is an isometric view of FIG. 10A with a section of an ionic electroactive polymer actuator indicated in solid lines to better reveal details of the components therein; and FIG. 10D is a side view of FIG. 10A with a section of an ionic electroactive polymer actuator indicated in solid lines to better reveal details of the components therein.

FIGS. 11A to 11E illustrate schematically the integration of the polymer sleeve to surround over the core, the proximal end of the ionic electroactive polymer actuator and the electrically-conductive wires, wherein:

FIG. 11A is an isometric view of an elongate, flexible portion and a bendable portion of a guidewire according to one embodiment, wherein the elongate, flexible portion comprises a core and a polymer sleeve surrounding the core 1 while the bendable portion includes an ionic electroactive polymer actuator 110b shown in FIGS. 6A and 6B; FIG. 11B is a side view of FIG. 11A, FIG. 11C is an isometric view of FIG. 11A with a section of a polymer sleeve indicated in solid lines to better reveal details of the components therein;

FIG. 11D is a side view of FIG. 11A with a section of a polymer sleeve indicated in solid lines to better reveal details of the components therein; and FIG. 11E is a side view of FIG. 11A with a section of a polymer sleeve and an ionic electroactive polymer actuator indicated in solid lines to better reveal details of the components therein.

DETAILED DESCRIPTION OF THE PREFERRED EMBODIMENTS

Figure 1A:
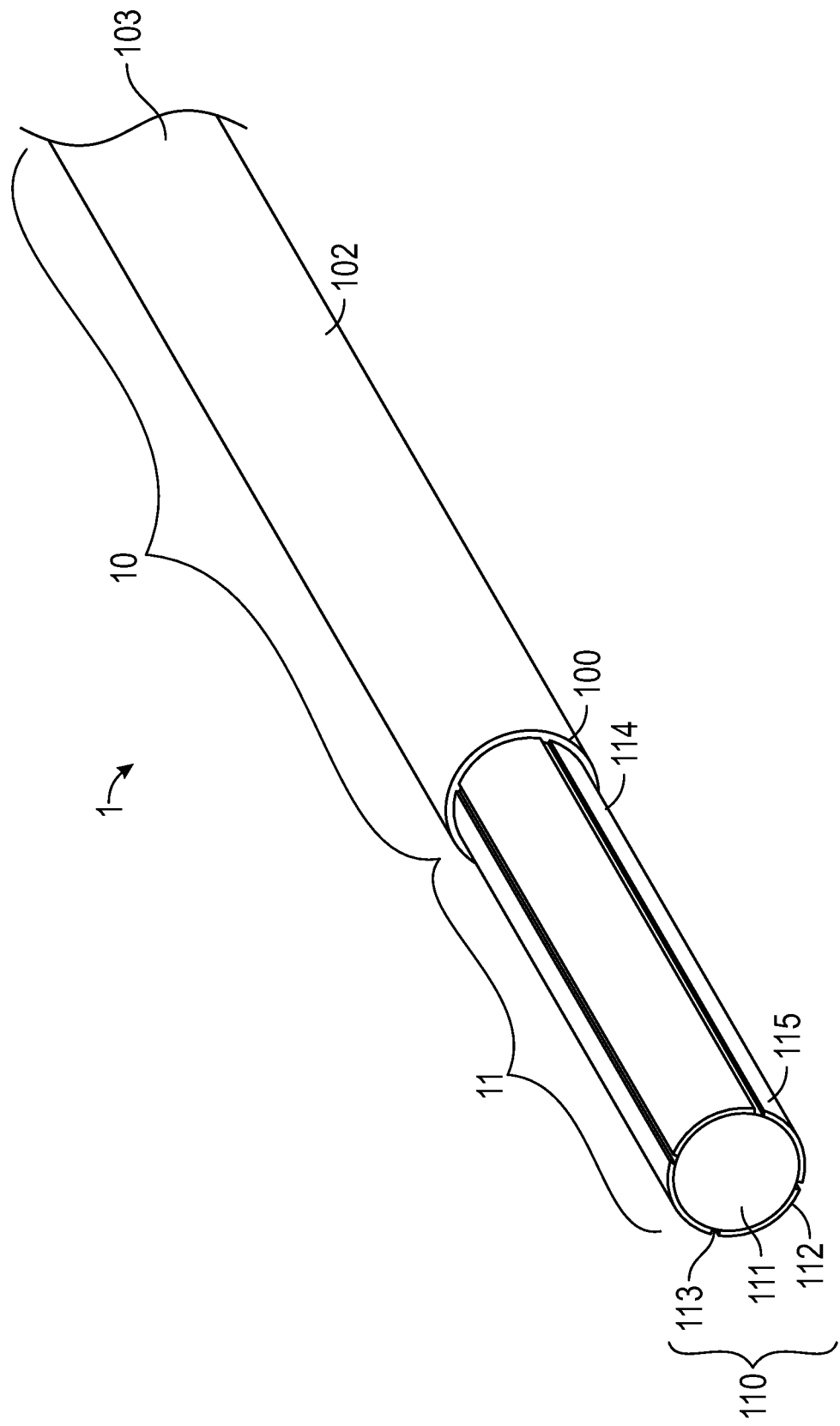
FIG. 1A is an isometric view of a portion of a guidewire comprising an elongate, flexible portion and a bendable portion according to one embodiment.

Medical devices such as guidewires are sufficiently slender to be inserted into a lumen such as an artery, a vein, a throat, an ear canal, a nasal passage, a urethra or any number of other lumens or bodily passages. These medical devices enable physicians to perform non-invasive surgery resulting in a substantially shortened recovery period as compared to conventional surgery by preventing the need to cut a substantial opening in a subject or a patient to provide local access for performing a surgical procedure or medical operation.

As used herein, the terms "subject" or "patient" refer to the recipient of a medical intervention with the device. In certain aspects, the patient is a human patient. In other aspects, the patient is a companion, sporting, domestic or livestock or other animal.

As used herein, the terms "ionic electroactive polymer actuator" refer to a component of a medical device comprising a thin polymer electrolyte member within which cations migrate in response to an electrical field imposed thereon, and one or more electrodes disposed on the surface of the polymer electrolyte member. As described herein, the "ionic electroactive polymer actuator" may be provided at the distal end in a bendable portion of a medical device to be responsible for moving or selectively bending the distal end thereof. More specifically, selective electrical energization of one or more electrodes causes the polymer electrolyte member or members to deform asymmetrically as a result of contraction along a side or portion of the polymer electrolyte member and/or swelling along a side or portion of the polymer electrolyte member. It will be understood that cations within the polymer electrolyte member will migrate towards an anodically energized electrode, and away from a cathodically energized electrode, while remaining within the matrix of the polymer electrolyte member. This causes a portion of the polymer electrolyte member adjacent to an anodically energized electrode to swell and a portion of the polymer electrolyte member adjacent to a cathodically energized electrode to contract, thereby causing the polymer electrolyte member to bend. Coordinated control of electrical signals delivered to the electrodes through electrically-conductive wires produces bending of the polymer electrolyte member in an intended or selected direction. In a relaxed or un-energized state, the polymer electrolyte member of the ionic electroactive polymer actuator remains in its original form.

As used herein, the term "polymer electrolyte member" refers to a layer, membrane, rod or component in any shape or form comprising a polymer host and an electrolyte solvent (e.g., water, an ionic liquid or the like). The polymer host comprises, for example, but not by way of limitation, fluoropolymers and intrinsically conducting polymers. For example, the polymer electrolyte member can comprise a porous polyvinylidene fluoride or polyvinylidene difluoride, a highly non-reactive thermoplastic fluoropolymer produced by the polymerization of vinylidene difluoride, and containing ionic liquid or salt water. Alternately, the polymer electrolyte can comprise a gel formed by polyvinylidene fluoride or polyvinylidene difluoride, propylene carbonate and an ionic liquid.

As used herein, the terms "electrically-conductive wire" or "electrically-conductive conduit" refer to a component that conducts electrical signals from a source of electricity to one or more of the plurality of electrodes to affect bending of the polymer electrolyte member, and may comprise a noble metal for superior chemical stability and corrosion resistance. For example, but not by way of limitation, the electrically-conductive wires or conduits that deliver potential to selected electrodes to actuate the polymer electrolyte member comprise highly conductive platinum, a platinum alloy, silver or a silver alloy, or they comprise gold or a gold alloy which, in addition to being chemically stable and corrosion resistant, is malleable and can be advantageously formed into very slender electrically-conductive wires with very low inherent resistance to bending.

Figure 1B:
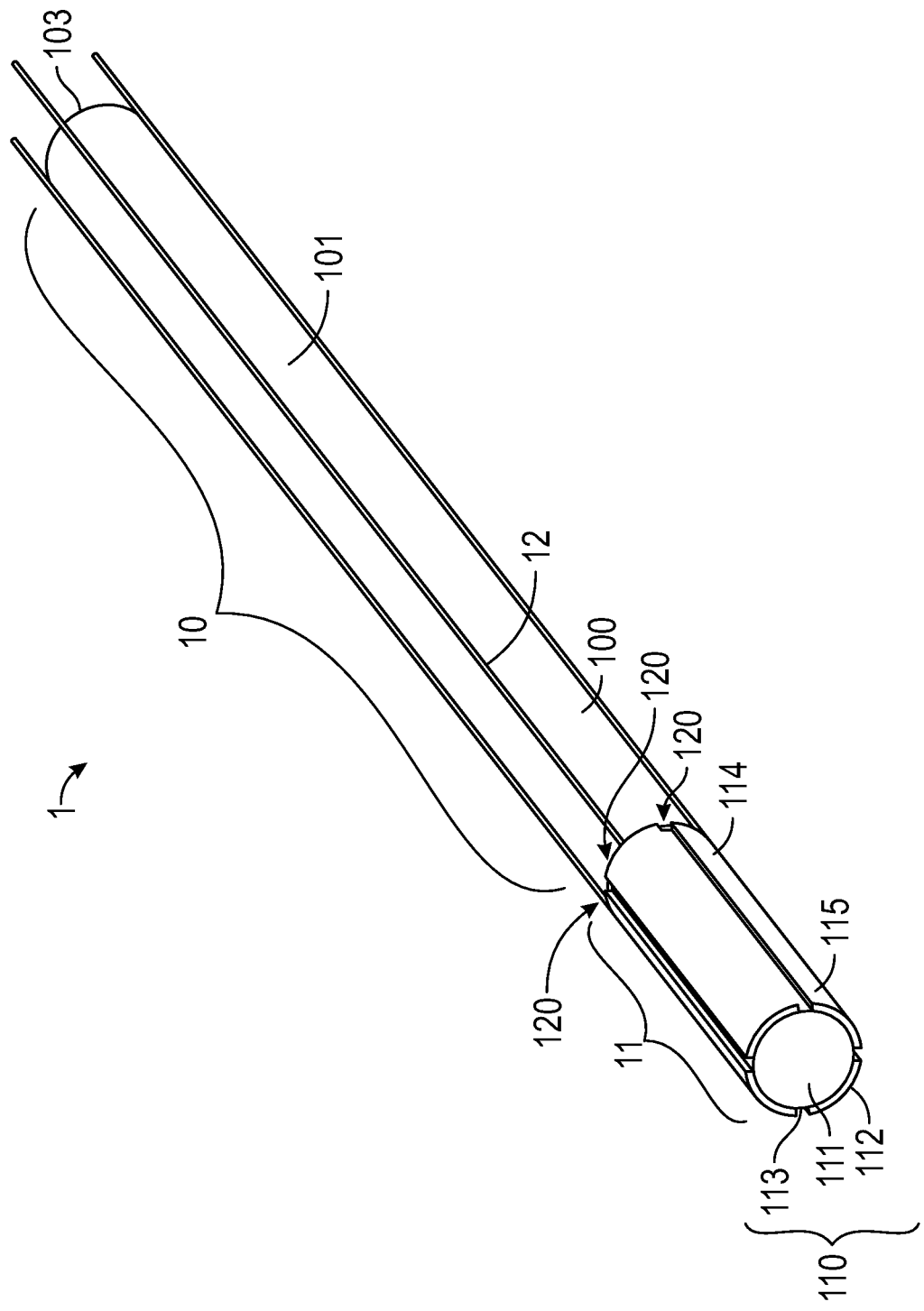
FIG. 1B is an isometric view of the portion of the guidewire of FIG. 1A according to one embodiment with a section of a polymer sleeve removed to reveal details of the components therein.

The following paragraphs describe certain embodiments of medical devices useful to perform, or to enable the performance of, surgical operations using the same, and methods that can be used to enable the preparation of such medical devices for same. It will be understood that other embodiments of medical devices and methods are within the scope of the claims appended herein below, and the illustration of such embodiments is not limiting of the present invention. FIG. 1A illustrates one embodiment of a medical device, comprising an isometric view of a portion of a guidewire 1. FIG. 1B is a perspective view of the portion of a guidewire 1 of FIG. 1A with the polymer sleeve removed to reveal details of the components therein. The guidewire 1 comprises an elongate, flexible portion 10 and a controllably bendable portion 11 disposed at the distal end 100 of the elongate, flexible portion 10. The elongate and flexible portion 10 further comprises a core 101 (see e.g., FIG. 1B) and a sleeve 102 surrounding the core 101. The bendable portion 11 includes an ionic electroactive polymer actuator 110 comprising a polymer electrolyte member 111 disposed adjacent to and generally collinear to the core 101 of the elongate, flexible portion 100 and centrally within a plurality of energizable electrodes 112 as they are positioned in FIGS. 1A and 1B. Each of the plurality of electrodes 112 that substantially surround the exterior surface 113 of the polymer electrolyte member 111 is connected to a distal end 120 of a different one of a plurality of electrically-conductive wires 12, through which an electrical signal or potential may be supplied to the so connected electrode 112.

Figure 2B:
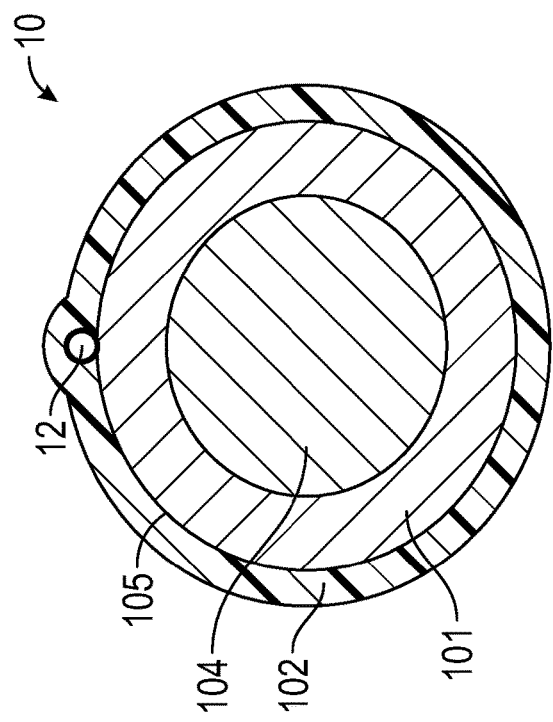
Figure 2A:
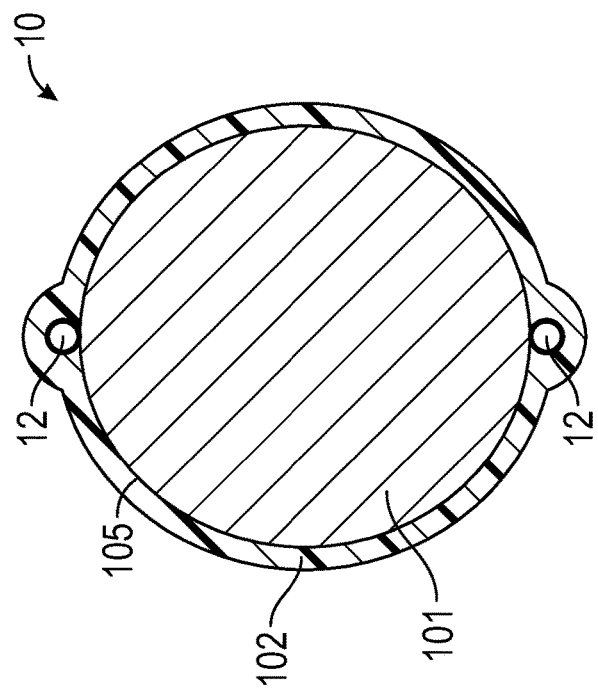
Figure 2C:
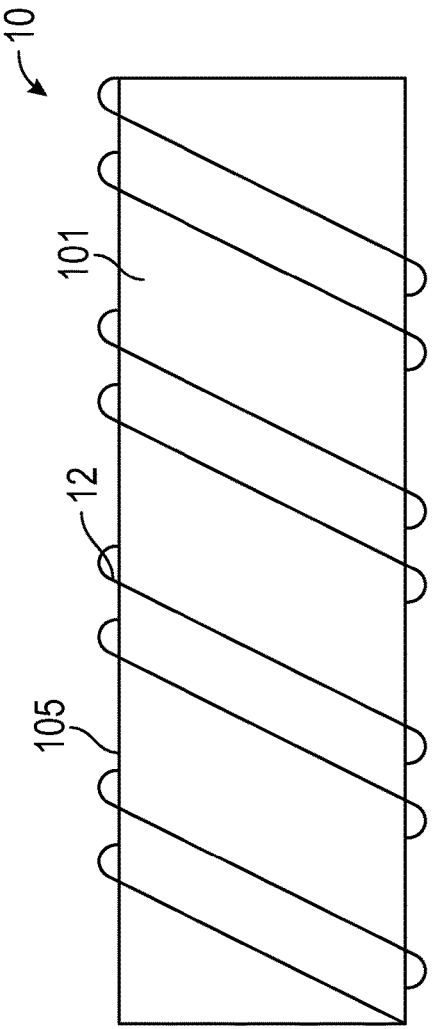
Figure 2D:
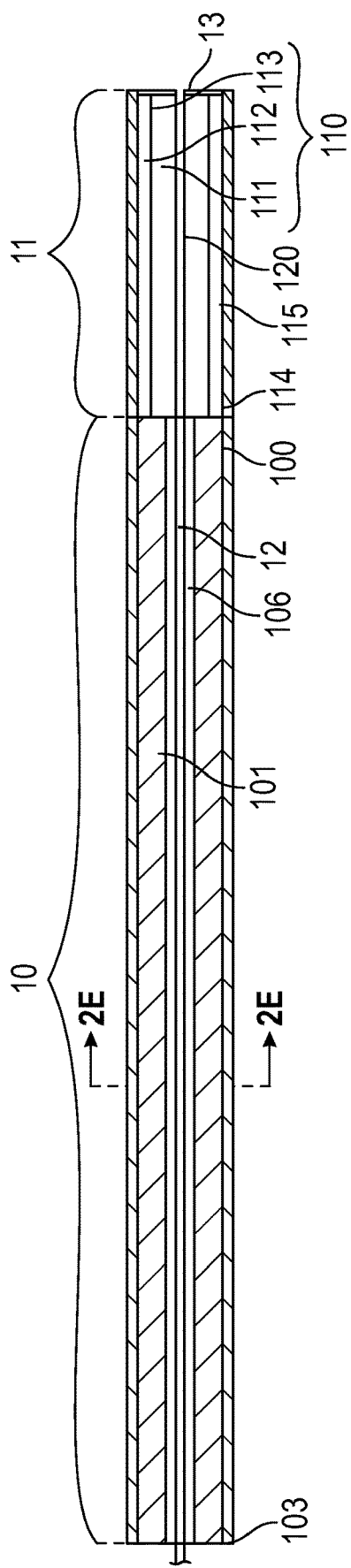
Figure 2E:
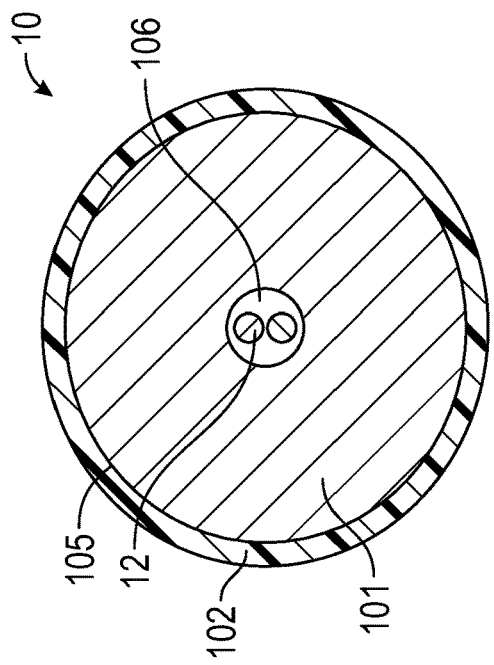

As shown in FIG. 1, the elongate and flexible portion 10 is extendable from an operable portion of a medical device which is provided at the proximal end 103 of the elongate and flexible portion 10 and available for manipulation by the operator (not shown. The core 101 of the elongate, flexible portion 10 is sufficiently slender to be inserted into a lumen (not shown) of a body (not shown). Also, the core 101 is sufficiently flexible and substantially axially incompressible so that it can be advanced through a lumen having a winding or tortuous pathway by pushing or driving the elongate, flexible portion 10 forward after it is introduced into the lumen of the body (not shown). The core 101 can include any suitable material including metals, metal alloys, polymers, or the like, or combinations or mixtures thereof. Some examples of suitable metals and metal alloys include stainless steel, such as 304 v stainless steel; nickel-titanium alloy, such as nitinol, nickel-chromium alloy, nickel-chromium-iron alloy, cobalt alloy, or the like; or other suitable material. The term "nitinol" herein is referred to a metal alloy of nickel and titanium. The entire core 101 can be made of the same material (e.g. nitinol), or in some embodiments, can include portions or sections made of different materials. In some embodiments, the material used to construct core 101 is chosen to impart varying flexibility and stiffness characteristics to different portions of shaft 101. For example, a proximal portion and a distal portion of core 101 may be formed of different materials (i.e., materials having different moduli of elasticity) resulting in a difference in flexibility of the core 101 at different locations thereof. In some embodiments, the material used to construct the proximal portion can be relatively stiff for pushability and torqueability (ability to twist without significant energy storage or hysteresis) of this portion of the core 101, and the material used to construct the distal portion can be relatively flexible by comparison for better lateral trackability and steerability of the distal portion of the core 101. For example, the proximal portion of the core 101 can be formed of straightened 304v stainless steel wire, and the distal portion of the core 101 can be formed of a straightened super elastic or linear elastic alloy (e.g., nitinol) wire. FIGS. 2A to 2F illustrate various embodiments of the elongate, flexible portion 10. In some embodiments, the core 101 has a solid cross-section (see FIGS. 2A, 2B, 2C and 2F). In the solid core embodiment of FIG. 2B, the core 101 is a metallic core wire comprising a solid metallic material 104. The core 101 having the solid metallic material 104 can couple to at least one of the electrodes 112 and serve as an additional electrically-conductive conduit to conduct electrical signals selectively sent from a source of electricity to one or more of the plurality of electrodes 112 to control bending of the polymer electrolyte member 111, so that the number of electrically-conductive wires 12 attached on the exterior surface 105 of the core 101 can be reduced accordingly, e.g. being reduced to one electrically-conductive wire 12 as compared with the two electrically-conductive wires 12 of FIG. 2A. In some alternative embodiments, the core 101 may have a hollow cross-section. For example, as shown in FIGS. 2D and 2E, an inner lumen 106 is formed within the core 101 along the elongate and flexible portion 10 for receiving the electrically-conductive wires 12.

A polymer sleeve 102 surrounds the core 101 and a portion of the ionic electroactive polymer actuator 110 to facilitate guidewire maneuverability within a body lumen or passage. The polymer sleeve 102 comprises, for example, a polymer such as a thermoplastic or thermosetting polymer. For example, the polymer sleeve 102 may comprise polyether block amide (PEBA), polyurethane, polyetherester, polyester, polyaryletherketone (PAEK) or linear low-density polyethylene, and the like, or copolymers or mixtures or combinations thereof. Additionally, the polymer sleeve 102 may comprise polymers such as polyamide, elastomeric polyamides, block polyamide/ethers, silicones, polyethylene, and the like, or mixtures, combinations, or copolymers thereof, or with any of the other materials listed above. In a preferred embodiment, the polymer sleeve 102 comprises PEBAX® (available from Arkema) or polytetrafluoroethylene (PTFE) or a combination thereof to provide relatively flexible polymeric properties for the sleeve 102. Some other suitable exemplary materials for the polymer sleeve 102 include nylon, polyetheretherketone (PEEK), polyimide (PI), polyetherimide (PEI), fluorinated ethylene propylene (FEP) and/or perfluoroalkoxy polymer resin (PFA). By employing careful selection of materials and processing techniques, thermoplastic, solvent soluble, and thermosetting variants of these and other materials can be employed to achieve the desired results such as flexibility, kink resistance or the like.

Additionally, in some embodiments, a coating, for example a lubricious (e.g., hydrophilic) or other type of coating may be applied over portions or all of the polymer sleeve 102, and/or other portions of the guidewire 1. Hydrophobic coatings such as fluoropolymers provide a dry lubricity which improves guidewire handling and device exchanges. Lubricious coatings improve steerability within a body lumen or passage, and improve lesion crossing capability therein. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. In a preferred embodiment, the polymer sleeve 102 is coated with a hydrophilic polymer as discussed above.

The electrically-conductive wires 12 are connected to the core 101 using any suitable connecting technique (e.g. mechanical fasteners (bolts or clamps), laser welding, ultrasonic bonding, brazing and soldering). For example, in FIGS. 2A and 2B, each of the electrically-conductive wires 12 is disposed linearly along the length of the exterior surface 105 of the core 101. Alternatively, each of the plurality of electrically-conductive wires 12 is helically or interweavingly wrapped around the exterior surface 105 of the core 101 as shown in FIG. 2C. Then, each of the electrically-conductive wires 12 of FIG. 2A to FIG. 2C is secured with respect to the polymer sleeve 102, the core 101 and at least a portion of the proximal end of the ionic electroactive polymer actuator 110. (see, e.g. FIG. 1A). In other embodiments, the electrically-conductive wires 12 can pass through the inner lumen 106 of FIG. 2D. In yet another embodiment, a plurality of grooves 107 as shown in FIG. 2F are formed to extend linearly along the exterior surface 105 of the core 101, each groove receiving one of the electrically-conductive wires 12 therein, respectively. The polymer sleeve 102 further covers the grooves 107 to enclose the electrically-conductive wires 12 therein.

Figure 3B:
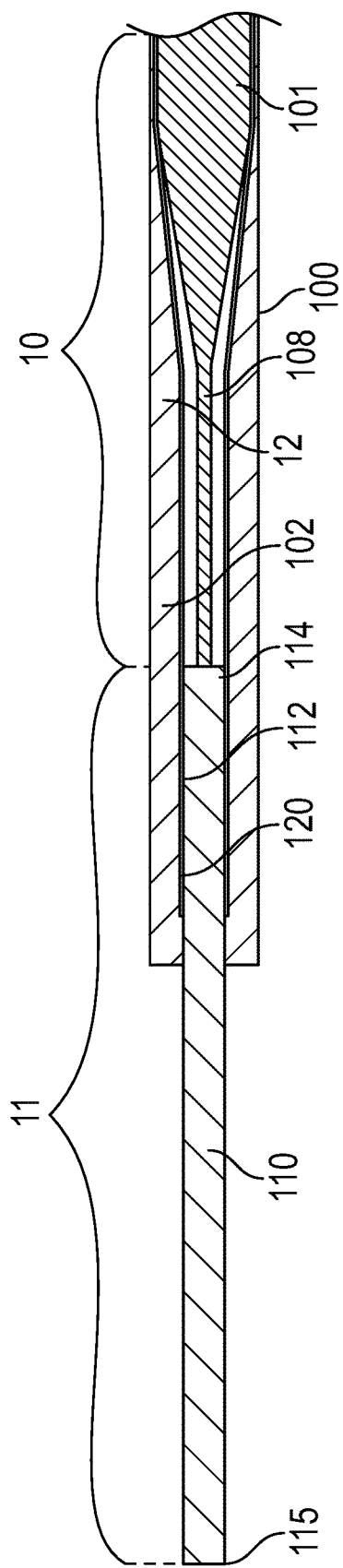
Figure 3C:
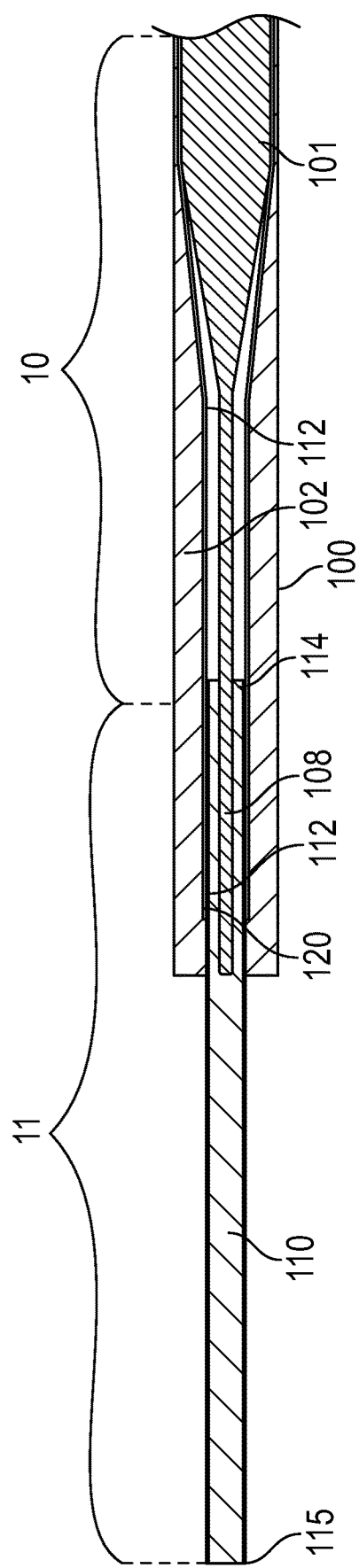

FIGS. 3A and 3B illustrate the elongate, flexible portion 10 and the bendable portion 11 of the guidewire 1 of FIG. 1A according to one embodiment where a tapered end 108 is provided adjacent to the distal end 100 of the core 101 of the elongate, flexible portion 10. The diameter of the core 101 includes a minor diameter portion extending from a transition to the distal end thereof, a major diameter portion extending from the transition to the proximal end thereof (not shown), and the transition transitions the core 101 diameter between the major to minor diameter portions along one or more tapers or steps. In some embodiments, as shown in FIG. 3A to 3B, the core 101 surrounded by the polymer sleeve 102 has a tapered portion 108 having a geometry that decreases in cross sectional area as the surface of the core becomes closer to the distal end 100 of the elongate, and the reduced cross section of the minor diameter portion of the core 101 at the distal end 100 contacts a surface of the proximal end 114 of the ionic electroactive polymer actuator 110. The polymer sleeve 102 is then formed by extruding any suitable polymer(s) as described above onto the core 101 and the proximal end 114 of the ionic electroactive polymer actuator 110 to firmly secure them together. Also, to be firmly interconnected, in other embodiments shown in FIG. 3C, the minor diameter portion extending from the tapered end 108 to the distal end 100 of the core is embedded in an opening provided therefor extending inwardly of the proximal end 114 of the polymer electrolyte member 111. In some embodiments, if tapered, the core 101 can include a uniform or a non-uniform transition of the tapered portion 108, depending on the transition characteristics desired. For example, the diameter transition surface profile of the tapered portion 108 of the core 101 may be linear, curvilinear, or step-wise, and can include more than one transition type or change in diameter. The angle of any such transition with respect to a centerline of the core can vary, depending upon the desired flexibility characteristics of the core 101. The length of the tapered portion 108 may be selected to obtain a more (longer length) or less (shorter length) gradual transition in stiffness along its length in the core 101. The tapered portion 108 of the core 101 may be tapered or shaped by any one of a number of different techniques known in the art, for example, by cylindrical grinding (e.g. outside diameter grinding or centerless grinding), but the tapering method is not limited to this.

Figure 4A:
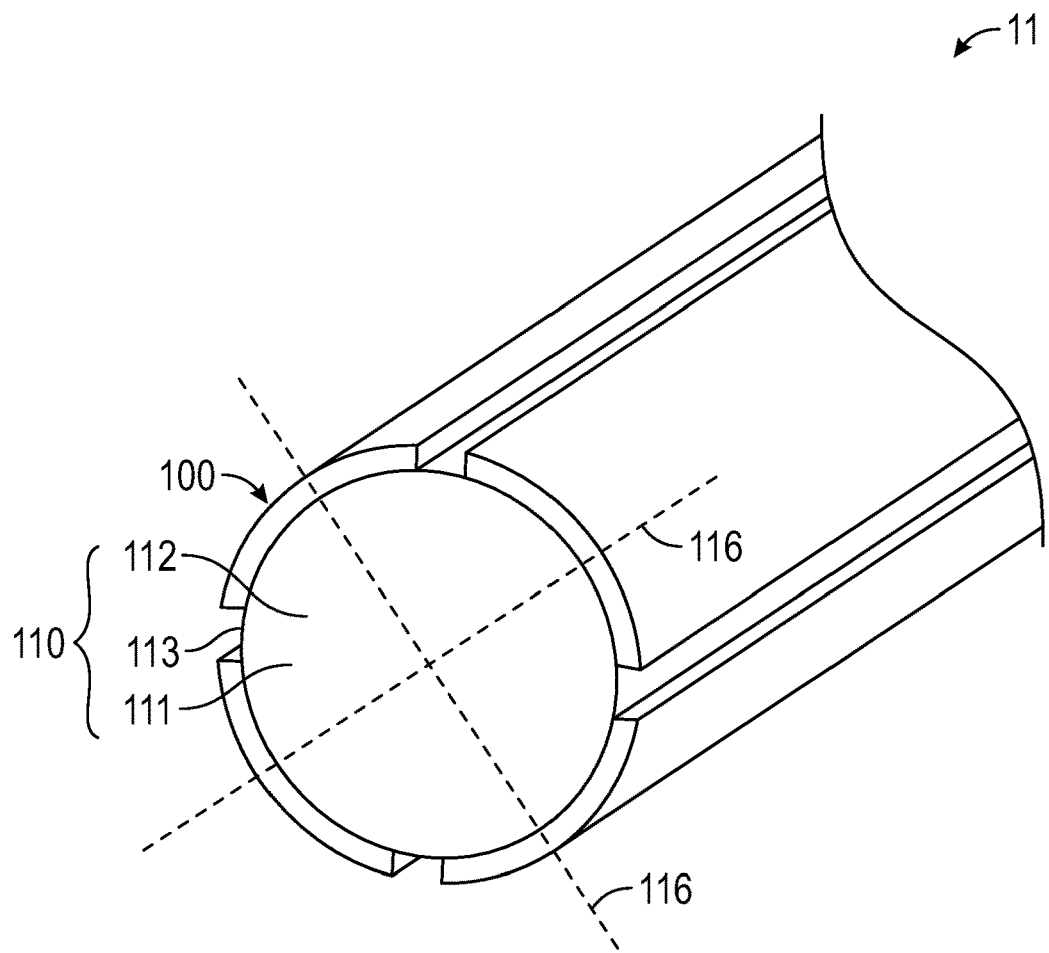
FIG. 4A is an isometric view of a portion of the bendable portion of one embodiment of FIGS. 1A and 1B, illustrating the bendable portion in the straight mode.

FIG. 4A is an isometric view of an end portion of the bendable portion 11 of the embodiment of the guidewire 1 of FIGS. 1A and 1B, illustrating the bendable portion 11 in the straight mode. The bendable portion 11 includes an ionic electroactive polymer actuator 110 comprising a rodlike polymer electrolyte member 111 disposed adjacent to the distal end 100 of elongate, flexible portion 10 FIGS. 3A to 3C and centrally to an angularly-distributed plurality of energizable electrodes 112 on the circumference thereof, i.e., the exterior surface 113. Each of the plurality of electrodes 112 that are laid out to surround the exterior surface 113 of the polymer electrolyte member 111 is connected to a distal end 120 of an electrically-conductive wire 12 through which an electrical signal or potential is selectively supplied to the connected electrode 112, and spaced from one another by a gap formed of a portion of the exterior surface 113 of the polymer electrolyte member 111. In one embodiment, the ionic electroactive polymer actuator 110 may comprise a plurality of angularly distributed electrodes 112 equi-angularly distributed about the exterior surface 113 of the polymer electrolyte member 111. For example, but not by way of limitation, the ionic electroactive polymer actuator 110, in the embodiment of FIG. 4A, comprises the polymer electrolyte member 111 and four angularly-distributed electrodes 112 that are separated or spaced apart along the exterior surface 113 of the polymer electrolyte member 111, one from the others by about 90 degrees (1.571 radians) between their centers or centerlines 116. As another example, but not by way of limitation, the ionic electroactive polymer actuator 110 may comprise eight angularly-distributed electrodes 112 that are separated along the exterior surface 113 of the polymer electrolyte member 111, between their centerlines, by about 45 degrees (0.785 radians). In yet another example, the ionic electroactive polymer actuator 110 may comprise three angularly-distributed electrodes 112 that are separated along the exterior surface 113 of the polymer electrolyte member 111, between their centerlines, one from the others by about 120 degrees (2.094 radians). It will be understood that each of the plurality of electrodes 112 occupies a circumferential span along the surface of the polymer electrolyte member, and that the "angular separation" may therefore be stated in terms of the centerlines of the electrodes instead of in terms of the adjacent edges of the electrodes, which will be much closer to the adjacent edge of the adjacent electrode. In some embodiments of the medical device, the electrodes are spaced in a manner to provide a substantial gap as insulation channels intermediate adjacent electrodes.

In one embodiment, the ionic electroactive polymer actuator 110 of FIG. 4A is an ionic polymer-metal composite (IPMC) actuator. In one embodiment, the ionic electroactive polymer actuator 110 comprises a polymer electrolyte member 111 made of PVDF-HFP that is impregnated with EMITF (as an electrolyte). Alternately, other embodiments of the ionic electroactive polymer actuator 110 of the guidewire 1 may include a polymer electrolyte member 111 that comprises a perfluorinated ionomer such as Aciplex™ (available from Asahi Kasei Chemical Corp. of Tokyo, Japan), Flemion® (available from AGC Chemical Americas, Inc. of Exton, Pa., USA), Fumapem® F-series (available from Fumatech BWT GmbH, Bietigheim-Bissingen, Federal Republic of Germany) or Nafion® (available from The Chemours Company of Wilmington, Del., USA.).

Figure 4B:
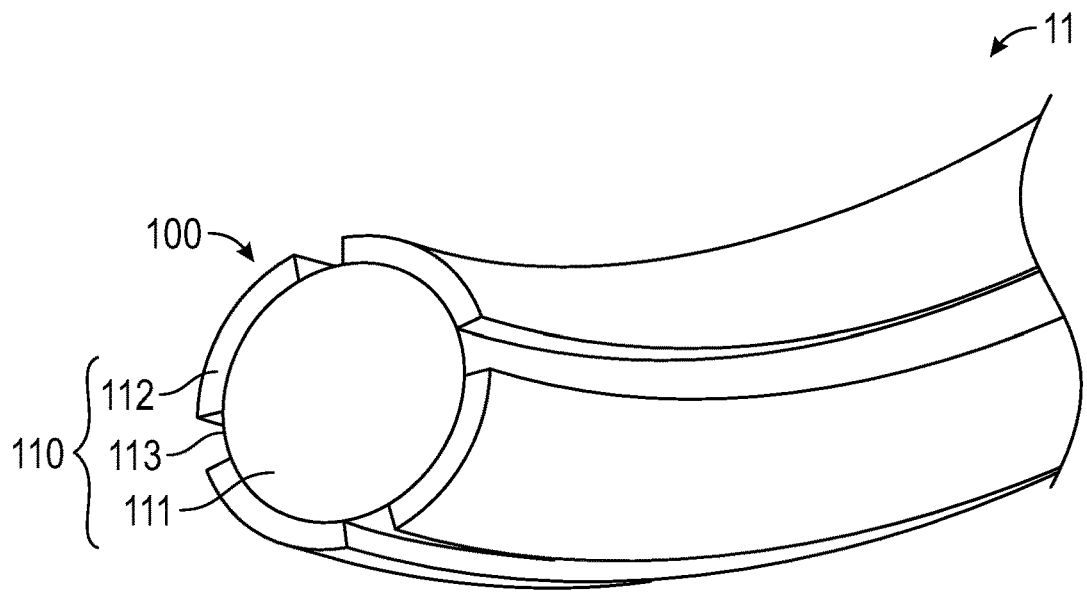
FIG. 4B is a perspective view of the portion of the bendable portion of FIG. 4A in the deformed or bending mode.

In one embodiment, the electrodes 112 may comprise one of platinum, gold, carbon-based material, or a combination (e.g. a composite) thereof. The carbon-material may comprise, for example but not limited to, carbide-derived carbon (CDC), carbon nanotube (CNT), graphene, a composite of carbide-derived carbon and the polymer electrolyte member 111, and a composite of carbon nanotube and the polymer electrolyte member 111. In an exemplary embodiment, the electrodes 112 are double-layered, comprising: a layer comprising a composite of carbon (CDC and/or CNT) and PVDF-HFP/EMITF and a gold layer. The electrodes 112 are integrated on the exterior surface 113 of the polymer electrolyte member 111 using any suitable techniques. For example, but not by way of limitation, metal electrodes 112 can be deposited (e.g. platinum or gold electrodes) thereon using an electrochemical process. Alternatively, the double-layered electrodes 112 can be prepared and integrated on the exterior surface 113 by the following steps: spraying a carbon-based material layer on the exterior surface 113, spray coating a gold layer on the carbon-based material layer, followed by integrating the carbon-based material layer and a gold layer using a reflow process. The detail of the reflow process is discussed in PCT Application No. PCT/US17/16513, which is fully incorporated herein by reference in its entirety. The bendable portion 11 is capable of being selectively and controllably deformed into a bent mode by selective energization of one or more of the plurality of electrodes 112, as will be explained in further detail below. FIG. 4B is a an isometric view of a portion of the bendable portion 11 of FIG. 4A in the deformed or bending mode. Each of the plurality of electrodes 112 is connected to a distal end 120 of an electrically-conductive wire 12 (FIG. 1B) through which an electrical signal may be applied to the electrode 112 to which the wire 12 is connected, thereby causing metal cations within the polymer electrolyte member 111 to move in a direction determined by the presence of a cathodic or anodic electrical potential selectively applied to individual ones of the electrodes 112. This cation migration produced by the applied electrical potential causes the polymer electrolyte member 111 to swell in the portion of the polymer electrolyte member 111 disposed proximal to an electrode supplied with the anodic potential and resultantly bend or warp in the direction of the remaining unswelled portion of the polymer electrolyte member 111. As a result, the magnitude and the direction of the bending deformation of the polymer electrolyte member 111 of the ionic electroactive polymer actuator 110 can be controlled by strategically selecting which of the electrodes 112 to energize and by adjusting the magnitude and sign (+ or −) of the electrical potential applied through the electrically-conductive wire 12 to the electrodes 112.

Alternately, in the event that the bendable portion 11 is observed to be in a deformed (bent) mode in the absence of the application of one or more electrical potentials to one or more of the plurality of the electrodes 112, the magnitude of the observed deflection can be determined by sensing the different electrical potentials imposed on different ones of the wires as a result of the bending, and equate those potential(s) to the extent of bending of the bendable portion 11 from a free state to a bent state by imposing the potentials electrically form a voltage source, to determine the magnitude and direction of an external force being applied to the bendable portion 11 or, alternately, in the event that the application of a known potential on the electrodes 112 fails to produce an anticipated deformation of the bendable portion 11, the difference between the anticipated deformation and the actual deformation (if any) can be used as an indicator of the magnitude of an external force applied to the bendable portion 11 of the guidewire 1.

FIG. 4C is a cross-sectional view of the bendable portion 11 of FIGS. 4A and 4B illustrating one embodiment wherein a first selected set of four electrical potentials are applied to four circumferentially distributed electrodes 112 disposed about the exterior surface 113 of the polymer electrolyte member 111 to provide two degrees of bending freedom (e.g. bending along X-axis direction and/or Y-axis direction). FIG. 4C illustrates the charge (sign) of the electrical potential applied to the plurality of angularly distributed electrodes 112 to impart bending of the bendable portion 11 in the direction of the arrow 2. It will be understood that the application of a positive potential on the electrodes 112 on the left and right sides of the bendable portion 11 of FIG. 4C, in addition application of a positive potential to the electrode 112 at the top of FIG. 4C, and further in addition to the application of a negative potential to the electrode 112 at the bottom of FIG. 4C, will result in a different amount of deformation than would occur as a result of the application of only a positive potential on the electrode 112 at the top of FIG. 4C and a negative potential imparted to the remaining electrodes 112. It will be understood that the user may select the plurality of electrical signals that produces the deformation desired by the user.

FIG. 4D is a cross-sectional view of the bendable portion 11 of FIGS. 4A and 4B revealing another embodiment wherein a second selected set of four electrical potentials are applied to the circumferentially distributed electrodes 112 disposed about the polymer electrolyte member 111. FIG. 4D illustrates the application of a positive potential to the electrode 112 at the top of the bendable portion 11 of FIG. 4D and also to the electrode 112 at the right side of the bendable portion 11 of FIG. 4D, and FIG. 4D further illustrates the application of a negative potential to the electrode 112 at the bottom of FIG. 4D and also to the electrode 112 at the left side of FIG. 4D. The deformation of the polymer electrolyte member 111 which results from the application of these electrical potentials is in the direction of the arrow 3.

It will be understood from FIGS. 4C and 4D that the bendable portion 11 of the guidewire 1 can be bent in multiple directions and with varying degrees of deformation or deflection by strategic control of the electrical charges imparted to each of the individual electrodes 112. Although the embodiment illustrated in FIG. 4A to 4D illustrates a bendable portion 11 including four electrodes 112, it will be understood that the bendable portion 11 of the actuation part 100 of the guidewire 1 may include fewer than four or more than four electrodes 112, and such other embodiments will have differing deflection and deformation directional capacities and thus provide more or less degree(s) of freedom.

FIG. 5 is an isometric view of the bendable portion 11 of the guidewire 1 according to another embodiment illustrating an ionic electroactive polymer actuator 110a where two circumferentially distributed electrodes are respectively disposed about the exterior surface 113a of the rodlike polymer electrolyte member 111a to provide one degree of freedom in bending motion (e.g. up or down. A top electrode 112a is disposed about the top of the exterior surface 113 of the rodlike polymer electrolyte member 111a and a bottom electrode 112a' is disposed symmetrically about the bottom of the exterior surface 113a. As described above, for example, the top portion of the polymer electrolyte member 111a adjacent to the energized top electrode 112a will contract (given the application of a positive potential to the top electrode 112a of FIG. 5), while the bottom portion of the polymer electrolyte member 111a adjacent to the energized bottom electrode 112a' will swell (given the application of a negative potential to the bottom electrode 112a'), thereby causing the polymer electrolyte member 111a to bend in the direction of the arrow 4.

Figure 6A:
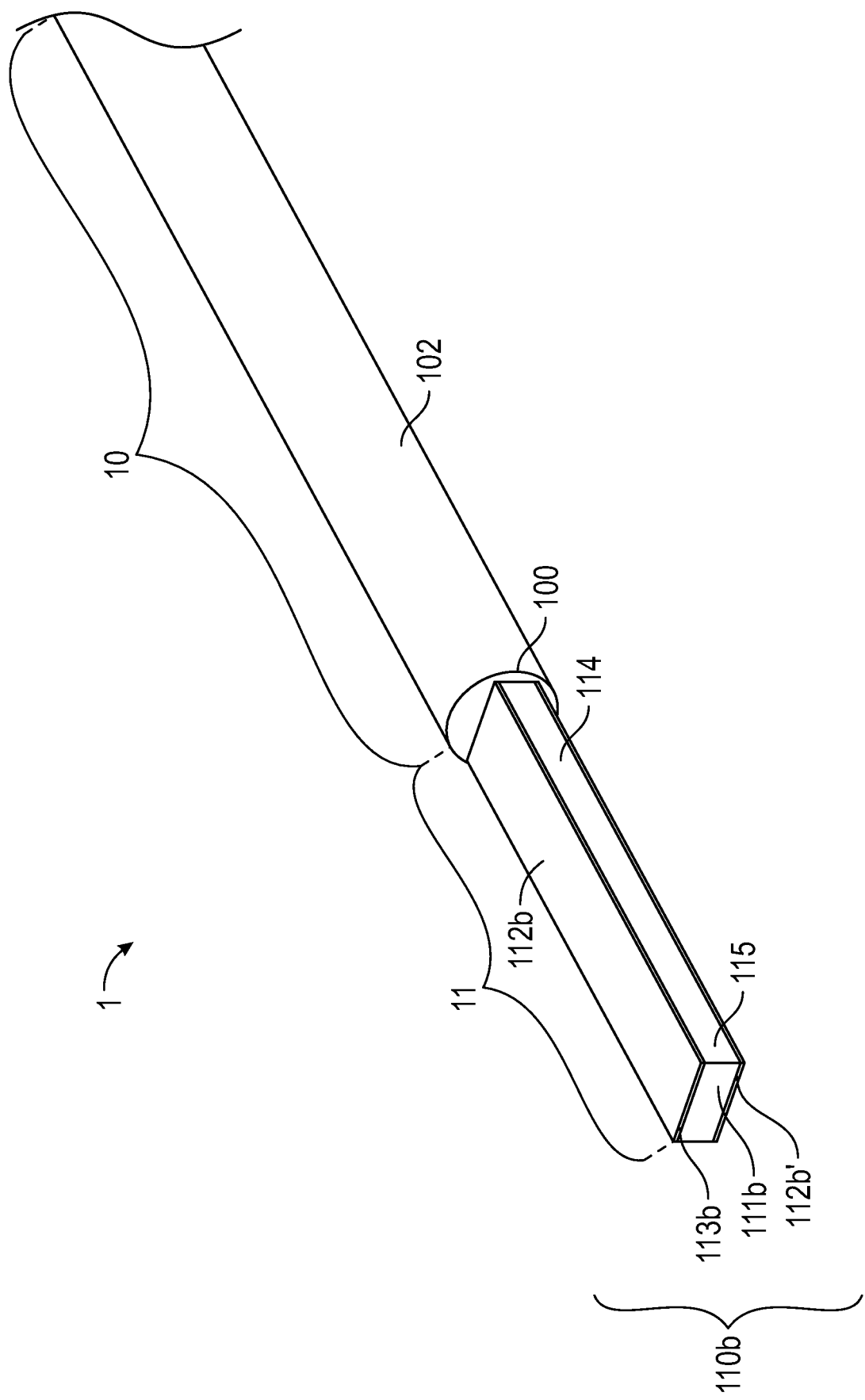
FIG. 6A is an isometric view of a guidewire comprising an elongate, flexible portion and a bendable portion according to another embodiment.
Figure 6B:
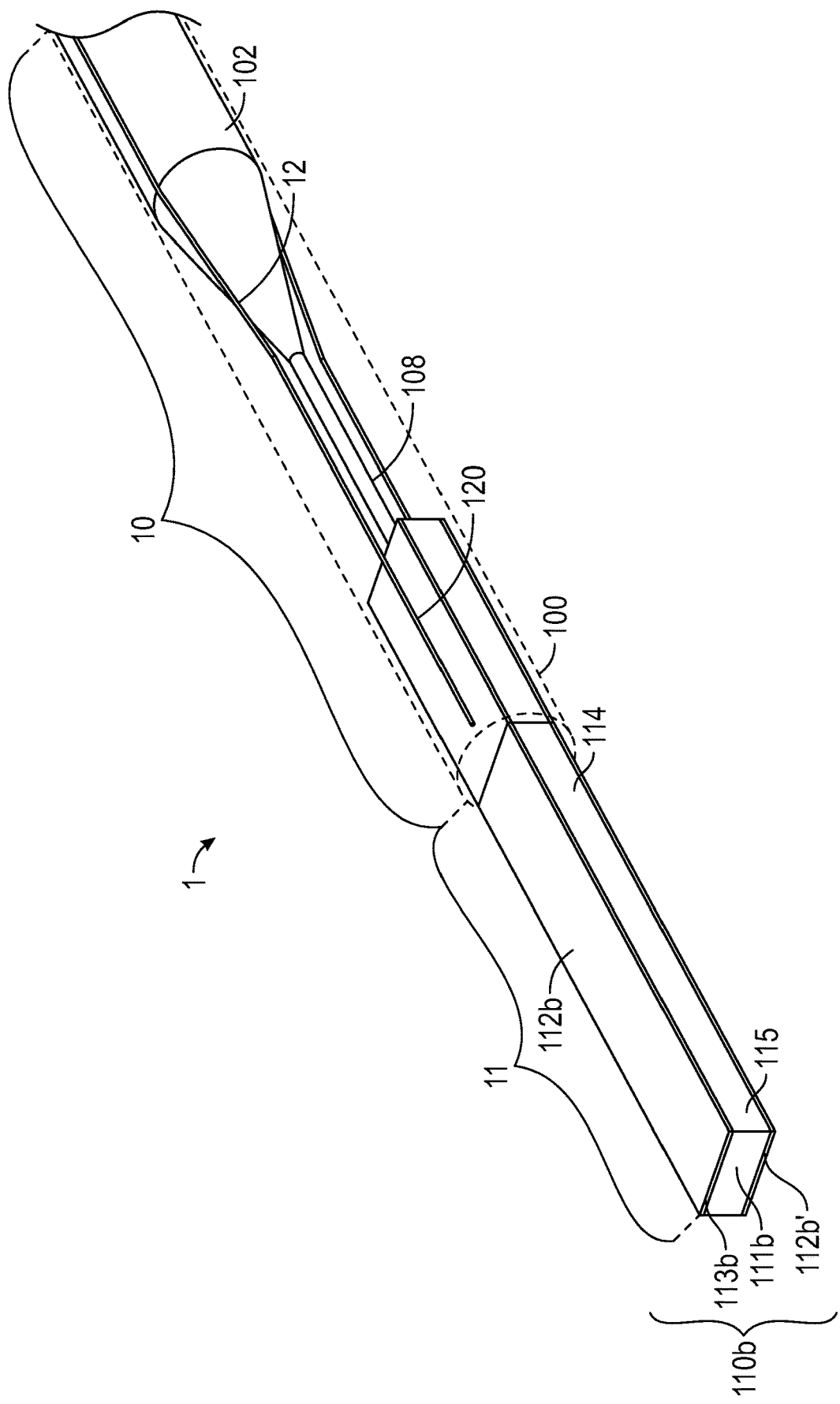
FIG. 6B is an isometric view of FIG. 6A with a section of a polymer sleeve indicated in solid lines to better reveal details of the components therein.
Figure 6C:
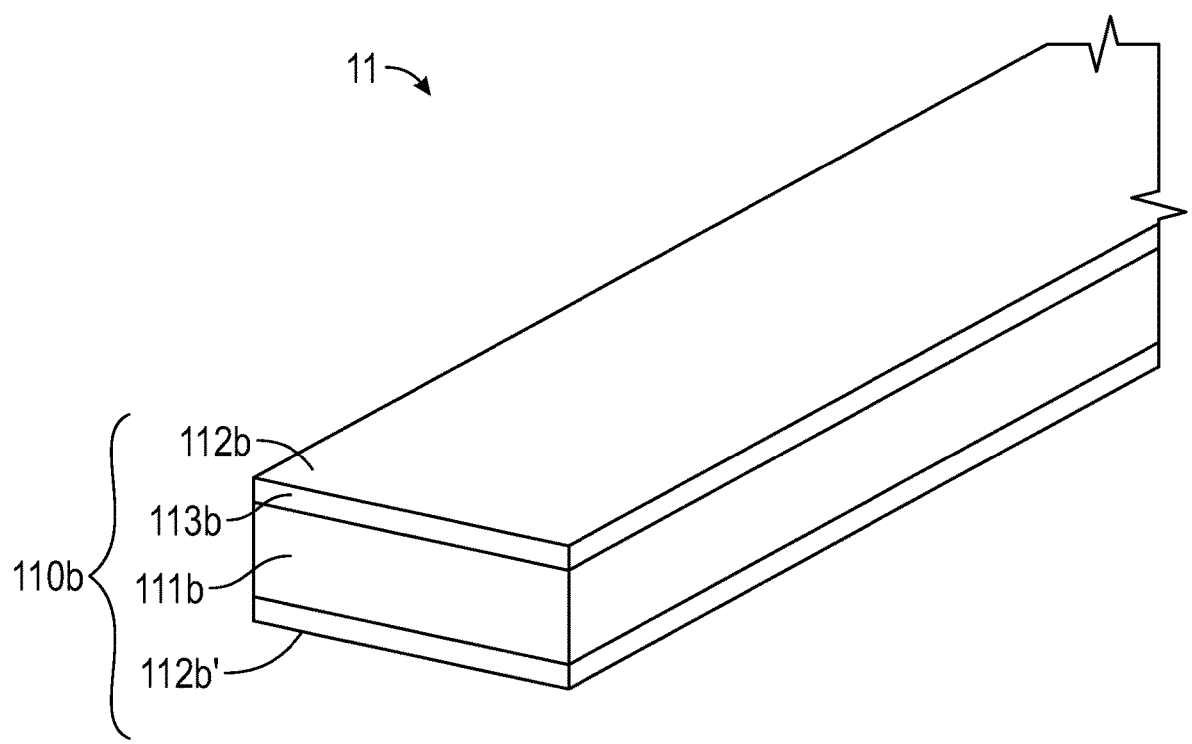
FIG. 6C is an isometric view of the bendable portion of FIGS. 6A and 6B illustrating a sandwich-structured ionic electroactive polymer actuator.

FIG. 6A illustrates another embodiment of a medical device, comprising an isometric view of a portion of a guidewire 1. FIG. 6B is an isometric view of the guidewire of FIG. 6A with an overlying polymer sleeve shown in phantom in FIG. 6B to reveal details of the components therein. The details related to the elongate, flexible portion 10 and the components thereof can be understood by reference to the above paragraphs. Compared with the above-described embodiments, the ionic electroactive polymer actuator 110b of the guidewire 1 of FIGS. 6A and 6B is provided herein in a different cross-sectional shape. For example, but not by way of limitation, in one embodiment, FIG. 6C is an isometric view of the bendable portion 11 of the guidewire 1 of FIGS. 6A and 6B illustrating a rectangular in cross section, or more specifically a "sandwich-structured" ionic electroactive polymer actuator 110b with two circumferentially distributed electrodes—a top electrode 112b and a bottom electrode 112b' which are respectively disposed about the top and the bottom exterior surface 113b of the rectangular in section polymer electrolyte member 111b to form a "sandwich" structure. The "sandwich-structured" ionic electroactive polymer actuator 110b can be prepared by any suitable techniques. For example, but not by way of limitation, the electrodes 112b, 112b' can be fabricated by casting thereof and then be assembled with the rectangular polymer electrolyte member 111b using heat-pressing without additional precise micromachining, thereby no gaps, which would form insulation channels, remaining between adjacent electrodes and the concomitant open circuit issues which may result from such processing. Similarly, the ionic electroactive polymer actuator 110b can bend as described in FIG. 5 to provide one degree of freedom in bending motion (e.g. up or down in Y-axis direction) when the top electrode 112b and the bottom electrode 112b' are energized with an electric potential of opposite sign or potential, i.e., + and −.

The electrically-conductive wires 12 are interconnected with the electrodes 112 using any suitable connecting techniques. For example, in the embodiment of FIGS. 3B and 3C, the electrically-conductive wires 12 are interconnected with at least a portion of each of the electrodes 112 (e.g. being integrated and embedded) at the proximal end 114 of the ionic electroactive polymer actuator 110 using conducting paste or laser welding. Then, the polymer sleeve 102 is overlayed on the core 101, a portion of the proximal end 114 and the electrically-conductive wires 12 connected thereto, to firmly secure them together.

FIG. 7A illustrates a side sectional view of the elongate, flexible portion 10 and the bendable portion 11 of the guidewire according to another embodiment. Here, a conductive bridge 13 is formed over the surface of the proximal end 114 of the ionic electroactive polymer actuator 110 to interface with the electrodes 112 and the polymer electrolyte member 111 and facilitate transmission of electrical signals therebetween. The electrically-conductive wire 12 is interconnected to the exterior surface 105 of the core 101 from the proximal end 103 (see, e.g. FIG. 1A) to the distal end 100 and a portion of the tapered end 108 of the elongate, flexible portion 10. The reduced diameter portion of the core 101 extending from the tapered portion to the distal end 100 thereof, and thus the distal end 120 of the electrically-conductive wire 12, is embedded into an opening provided in the polymer electrolyte member 111 and where the conductive bridge 113 extends inwardly of the opening into which the reduced diameter extends, a greater area of contact between the conductive bridge 13 and the wire 12 can be achieved. The tip of the distal end 100 of the reduced diameter portion may be spaced from the terminal end of the opening in the polymer electrolyte member as shown in FIGS. 7A and 7B, or may be grounded thereagainst. The conductive bridge 13 can be prepared by applying any conductive foil or tape made of metallic materials (e.g. gold, silver or copper) or non-metallic materials comprising conductive polymers onto the surface of the electrodes 112 and the polymer electrolyte member 111 using any suitable techniques (e.g. using adhesives, coating, plating, etching or depositing, but not limited to this). Then, as shown in FIG. 7B, the polymer sleeve 102 (shown in phantom) overlaying the core 101 and a portion of the proximal end 114 of the ionic electroactive polymer actuator 110 and the electrically-conductive wires 12 connected thereto, firmly secures them together.

FIG. 8A illustrates a sectional side view of the elongate, flexible portion 10 and the bendable portion 11 of the guidewire 1 having generally the same configuration as that shown in, and described herein with respect to, FIG. 2D according to one embodiment. FIG. 8B illustrates a sectional side view of the bendable portion 11 of FIG. 8A. An inner lumen 106 is formed within the core 101 over the length of the elongate and flexible portion 10 and a corresponding lumen extends into a portion of the polymer electrolyte member 111 at the proximal end 114 thereof. In FIG. 8B, individual conductive bridges 13a are shown provided at the distal end 115 of ionic electroactive polymer actuator 110 to electrically connect together the electrodes 112 and polymer electrolyte member 111, with the electrically-conductive wires 12 passing through the inner lumen 106 and embedded into the polymer electrolyte member 111 from the proximal end 114 to the distal end 115 thereof, thereby electrically connecting to the conductive bridges 13a using conventional wire bonding techniques such as soldering, crimping, stapling, pinching, welding, conductive adhesive (e.g., using conductive epoxy), and the like.

Referring back to FIGS. 6A and 6B, the "sandwich-structured" ionic electroactive polymer actuator 110b can be prepared by the following exemplary method. The polymer electrolyte member 111b is fabricated by first dissolving a fluoropolymer resin (e.g. poly(vinylidene fluoride-co-hexafluoropropylene (P(VDF-HFP)) in appropriate solvent such as acetone, dimethylacetamide (DMAc) or the like. The obtained PVDF-HFP formulation is then cast on a Polytetrafluoroethylene (PTFE) substrate using a Doctor blade method and cured at room temperature. Additionally, the PVDF-HFP film is dried under vacuum at 80 C to remove solvent residues. Finally, the PVDF-HFP film is heat-pressed between two PTFE plates and annealed at 200-240 C for 2 hours. After cooling down to room temperature, the PVDF-HFP film is peeled off from the PTFE substrate. The final film thickness is around 50-60 um. Next, the polymer film is impregnated with appropriate ionic liquid electrolyte, such as 1-Ethyl-3-methylimidazolium bis(trifluoromethylsulfonyl)imide (EMI MTFSI) or 1-Ethyl-3-methylimidazolium trifluoromethanesulfonate (EMITF) at 60-90 C for at least 12 hours.

Then, the top electrode 112b and the bottom electrode 112b' are respectively disposed about the top and the bottom exterior surface 113b of the obtained polymer electrolyte member 111b according to the following exemplary embodiment. Carbon-polymer composite used for the layered top electrode 112b and bottom electrode 112b' is fabricated by preparing a dispersion containing a desired conductive carbon material, PVDF-HFP and ionic liquid in a solvent (e.g. dimethylacetamide (DMAc)). Conductive carbon material used herein may be carbide-derived carbon (CDC), carbon nanotubes, carbon aerogel, graphene or other carbon allotrope or the combination thereof. The carbon-polymer mixture is stirred at elevated temperature for 4 hours to achieve homogenous dispersion. Then, the dispersion is treated with ultrasonic bath and ultrasonic probe for 4 hours. Thereafter, the obtained carbon dispersion is cast on a PTFE substrate using a Doctor's blade method and dried at room temperature for at least 14 hours. After that, the film is dried under vacuum at 80 C for 5 hours. Finally, the carbon-polymer composite film is heat-pressed at 200-240 C for 10-30 min.

The electrical conductivity of the obtained carbon-polymer composite film is often inadequate to provide proper electromechanical performance for the ionic electroactive polymer actuator 110b due to the type of carbon material used. Thus, in some embodiments, a thin gold foil with a thickness of 100-150 nm may be coated over the obtained carbon-polymer composite film to serve as a conductive current collector and increase the electrical conductivity of the electrode. Alternatively, in other embodiments, the carbon-polymer composite film may be covered with a gold nanoparticle dispersion coating using a spray-coating process to form the top electrode 112b and the bottom electrode 112b'.

Finally, the obtained polymer electrolyte member 111b, the top electrode 112b and the bottom electrode 112b' are assembled using heat-pressing at 200-240 C for 2-8 min, depending on the type of carbon material and electrode configuration used, to form the "sandwich-structured", laminated ionic electroactive polymer actuator 110b. In some embodiments, the total thickness of the ionic electroactive polymer actuator 110b is around 90-110 um. To be used in the bendable portion 11 of the guidewire 1, in one embodiment, the obtained ionic electroactive polymer actuator 110b may be cut into a 300 um wide strip with a length of 12 mm.

Figure 9A:
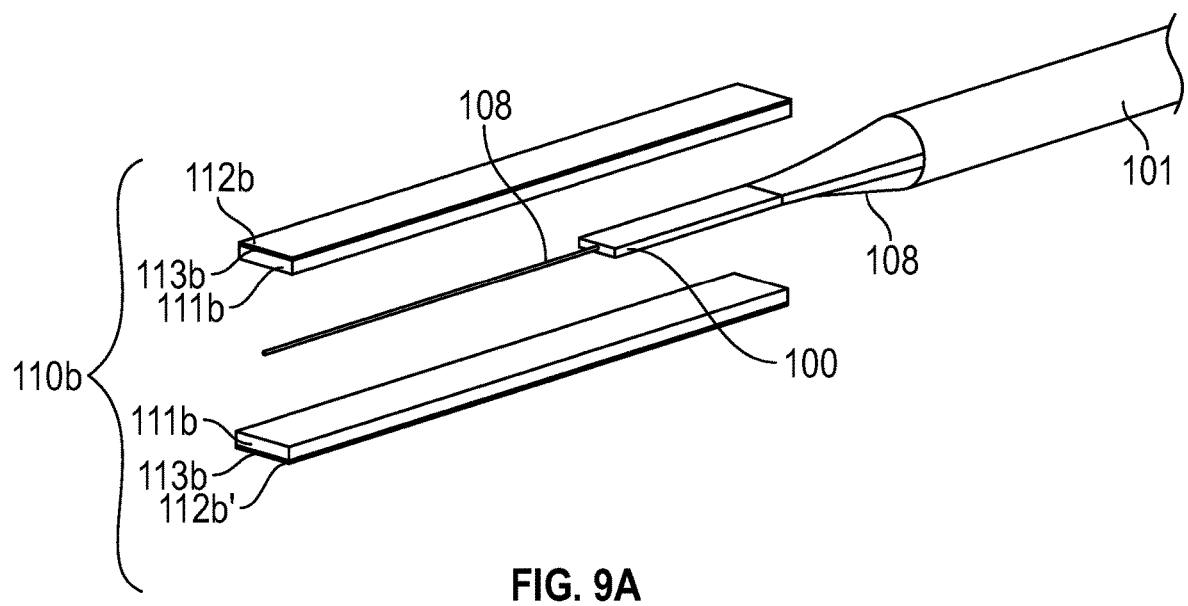
Figure 9B:
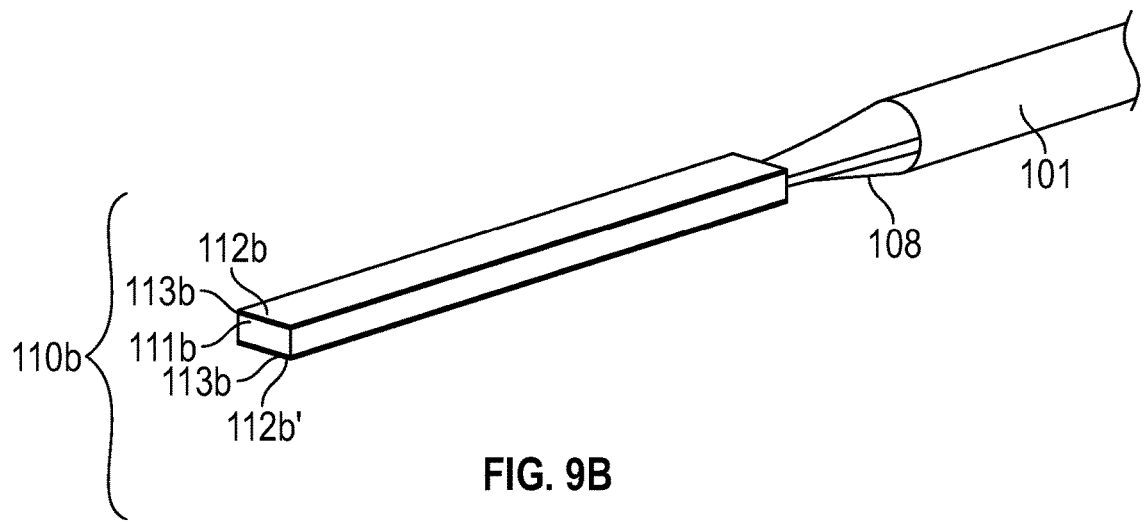
Figure 9C:
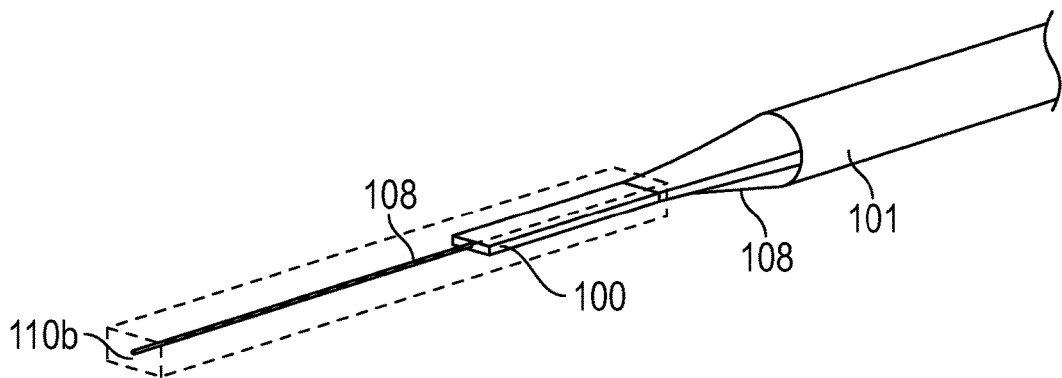

A process for manufacturing a guidewire shown in FIGS. 6A and 6B is illustrated as shown in FIGS. 9 to 11. FIGS. 9A to 9C illustrate schematically the integration of the ionic electroactive polymer actuator 110b and the reduced width portion of the core 100 distal to the tapered portion 108 at the distal end 100 of the core 101 of the elongate, flexible portion 10. FIG. 9A is an exploded view showing a core 101 and an ionic electroactive polymer actuator 110 of the guidewire shown in FIGS. 6A and 6B. FIG. 9B is an isometric view of the core 101 and ionic electroactive polymer actuator 110 of the guidewire shown in FIGS. 6A and 6B assembled on the core 101. FIG. 9C is a perspective view of FIG. 9B with a section of the ionic electroactive polymer actuator 110 shown in phantom to better reveal details of the components therein. As shown in FIG. 9A, a top electrode 112b and a bottom electrode 112b' are respectively disposed about the top and the bottom exterior surfaces 113b of the rectangular polymer electrolyte member 111b, at a rectangular in section reduced width portion of the core extending distally of the tapered portion 108 of the core 101. In FIGS. 9B and 9C, the reduced width portion and a portion of the tapered portion 108 of the core are then sandwiched between two rectangular polymer electrolyte member 111b using any suitable technique (e.g. heat pressing, reflowing or the like) to form a laminated "sandwich" structure.

Figure 10A:
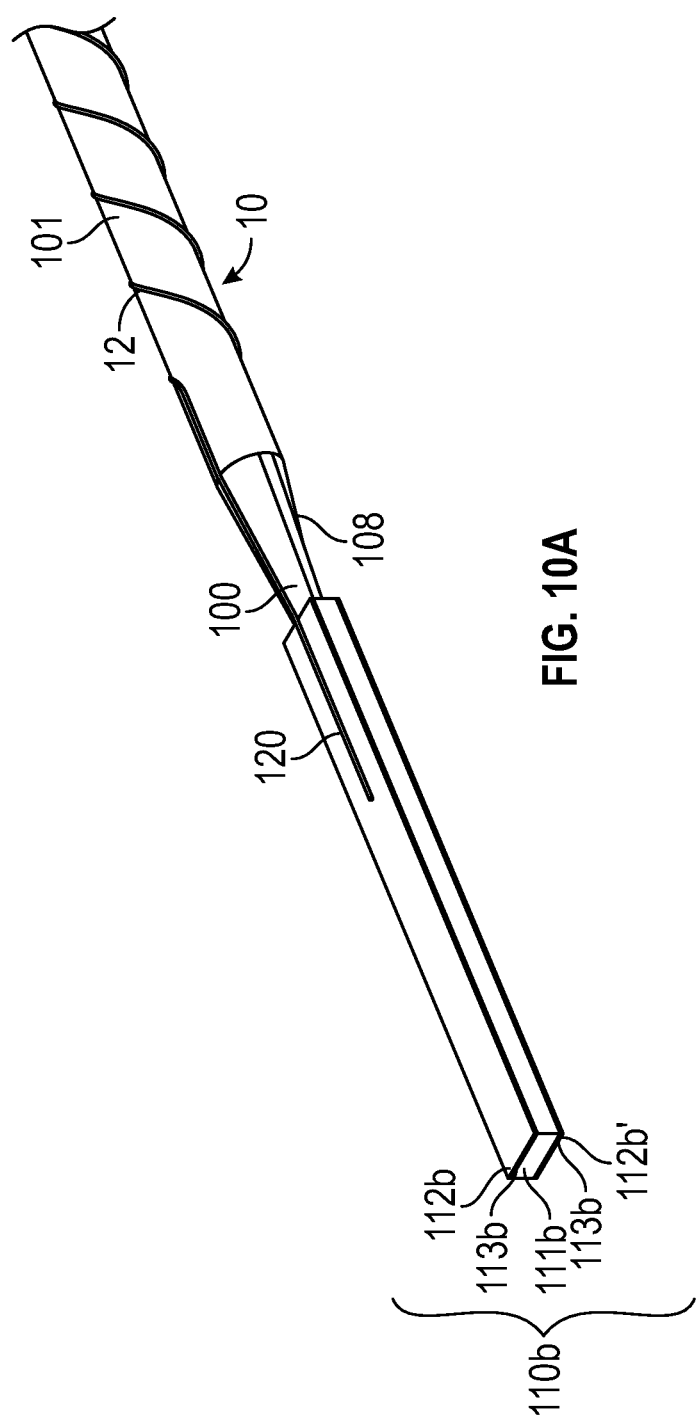
Figure 10B:
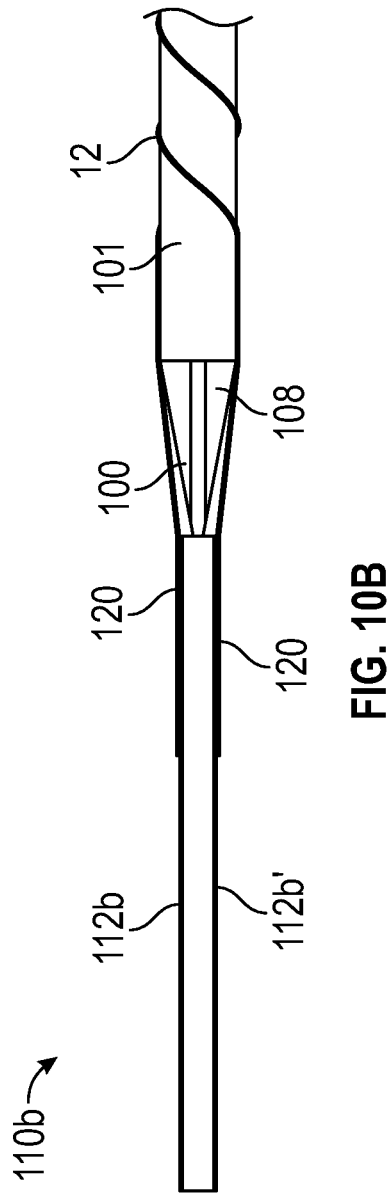
Figure 10C:
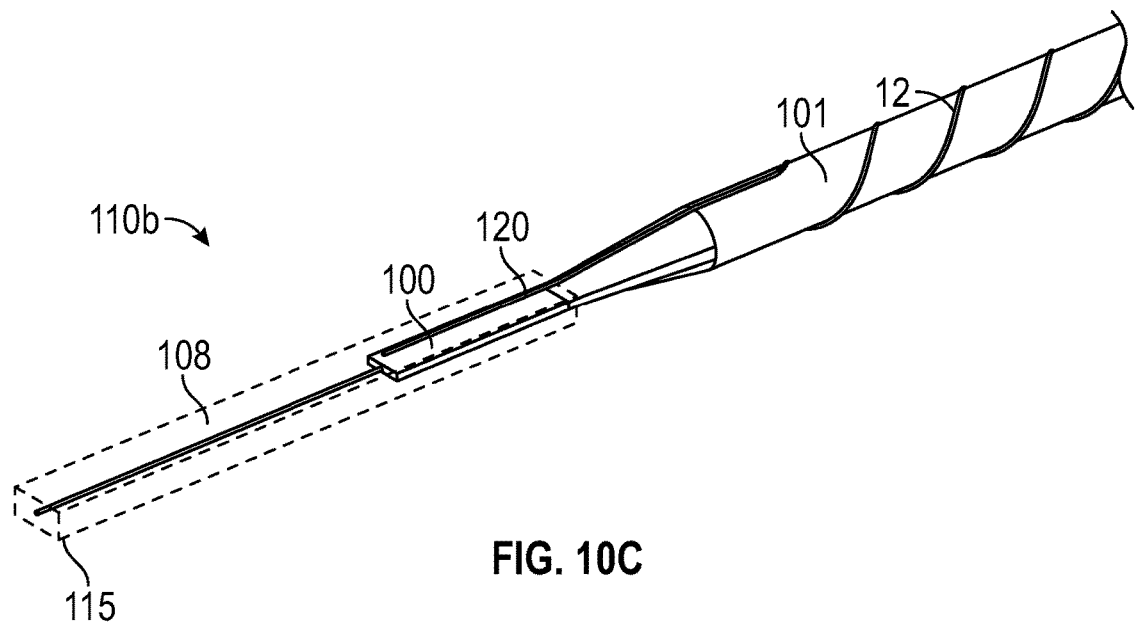
Figure 10D:
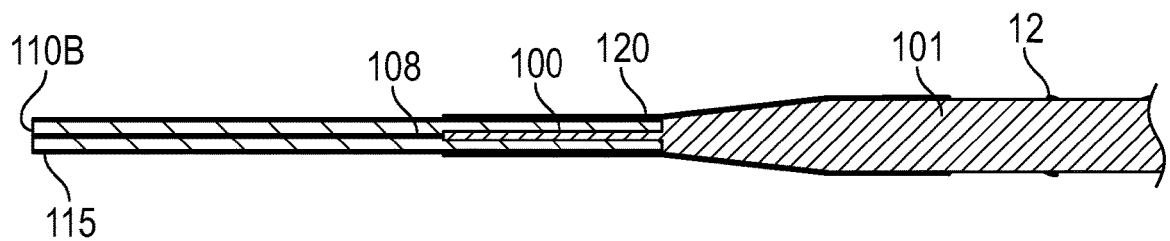

FIGS. 10A to 10D schematically illustrate the connection of the electrically-conductive wires 12 to the electrodes 112b, 112b' of the ionic electroactive polymer actuator 110b and the core 101 of the elongate, flexible portion 10. FIG. 10A is perspective view of a core, an ionic electroactive polymer actuator and the electrically-conductive wires of a guidewire according to one embodiment. FIG. 10B is a side view of FIG. 10A. FIG. 10C is a perspective view of FIG. 10A with the ionic electroactive polymer actuator shown in phantom to better reveal details of the components therein. FIG. 10D is a side view of FIG. 10A with the ionic electroactive polymer actuator shown in phantom to better reveal details of the components therein. Here, the electrically-conductive wires 12 shown in FIG. 10A to 10D are wound over the core 101 from the proximal end 103 to the distal end 100 thereof, and then the distal end 120 of each of the electrically-conductive wires 12 is interconnected to a surface of a single one of the electrodes 112b, 112b' using any suitable connecting technique (e.g. conducting paste or laser welding). In some embodiments, the reduced diameter portion of the core 101 distal of the tapered portion 108 is further embedded into the distal end 115 of ionic electroactive polymer actuator 110b to be better secured thereto, as shown in FIGS. 100 and 10D.

Figure 11C:
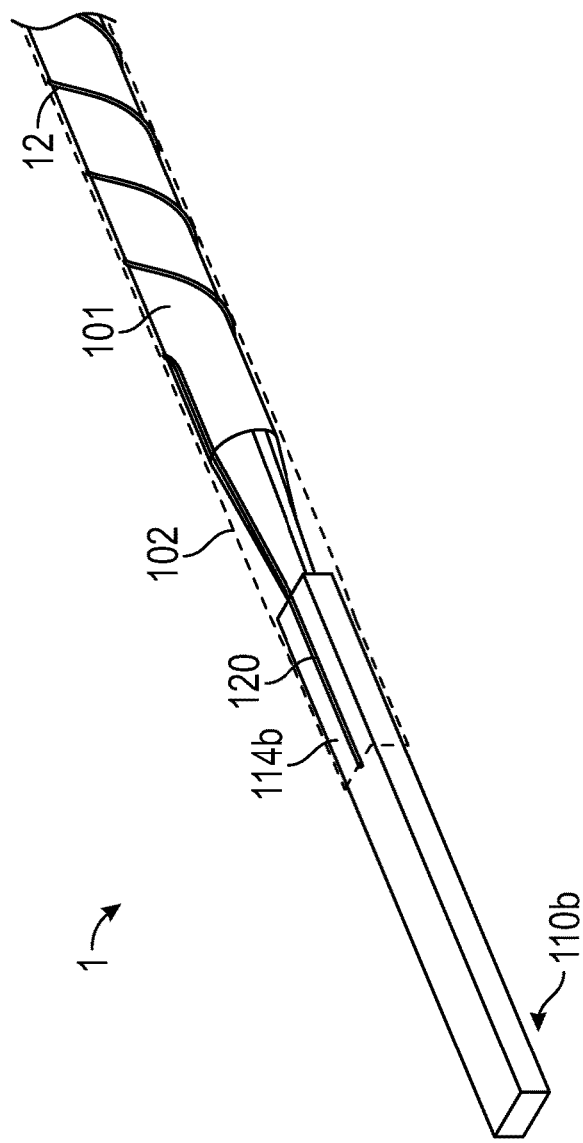
Figure 11D:
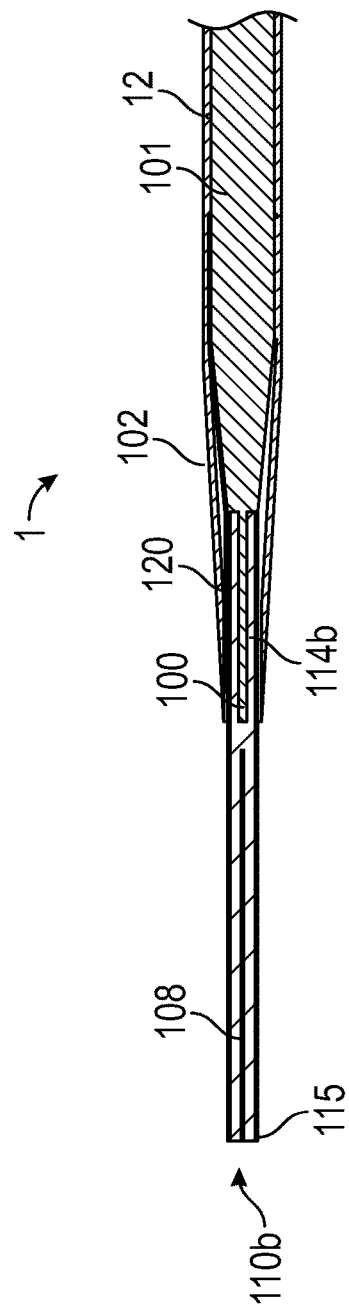
Figure 11E:
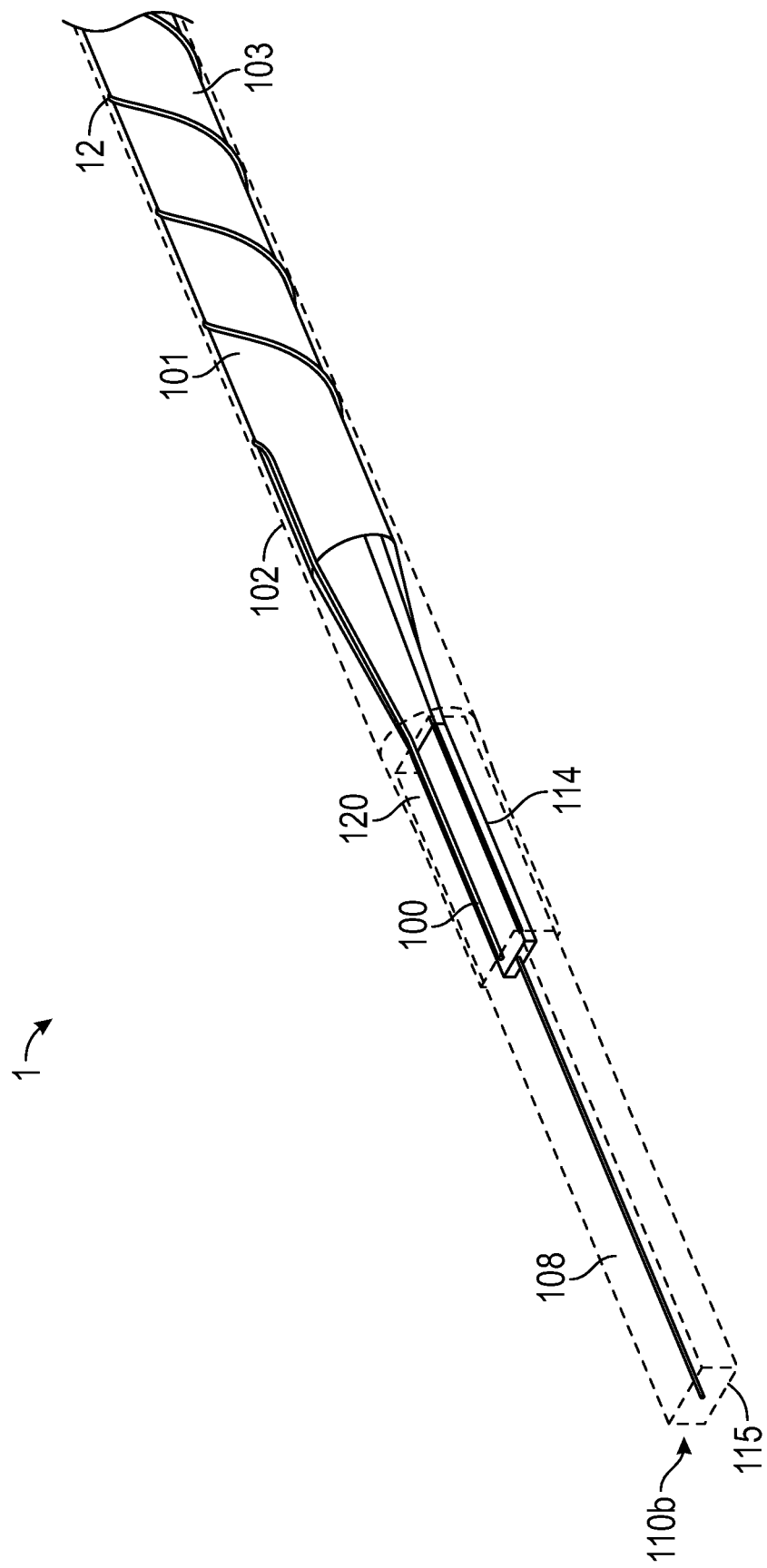

FIGS. 11A to 11E illustrate schematically the integration of the polymer sleeve 102 over the core 101, the proximal end 114b of the ionic electroactive polymer actuator 110b and the electrically-conductive wires 12. FIG. 11A is an isometric view of an elongate, flexible portion 10 and a bendable portion 11 of a guidewire according to one embodiment, wherein the elongate, flexible portion 10 comprises a core 101 (see e.g., FIGS. 11C and 11D) and a polymer sleeve 102 surrounding the core 101 while the bendable portion 11b includes an ionic electroactive polymer actuator 110b as described above (see. e.g. FIGS. 9-10). FIG. 11B is a side view of FIG. 11A. FIG. 11C is an isometric view of FIG. 11A with a section of a polymer sleeve shown in phantom to better reveal details of the components therein. FIG. 11D is a side view of FIG. 11A with a section of a polymer sleeve indicated in solid lines to better reveal details of the components therein. FIG. 11E is a side view of FIG. 11A with a section of a polymer sleeve and an ionic electroactive polymer actuator shown in phantom to better reveal details of the components therein. As shown in FIG. 11A to 11E, a polymer sleeve 102 is further provided to surround the core 101, a portion (i.e. the proximal end 114) of the ionic electroactive polymer actuator 110b and the electrically-conductive wires 12 thereon to facilitate guidewire maneuverability. The polymer sleeve 102 may be formed by extruding any suitable polymers as described herein onto the core 101 and the proximal end 114b of the ionic electroactive polymer actuator 110b to firmly secure them together. Then, a parylene coating (not shown) can be further applied to the outer surface of the resulting integrated guidewire 1 to provide the final moisture and dielectric barrier protection. The parylene coating also helps to provide biocompatibility and excellent lubricity over the entire length of the guidewire 1.

It is to be noted that various modifications or alterations can be made to the above-described exemplary embodiments of the invention without departing from the technical features of the invention as defined in the appended claims.

We claim:
1. A medical device, comprising:
at least one ionic electroactive polymer actuator, the actuator comprising:
at least one polymer electrolyte member defining at least a surface; and
a plurality of electrodes disposed about the surface of the at least one polymer electrolyte member;
an elongate, flexible portion defining a proximal end and a distal end secured adjacent to the ionic electroactive polymer actuator and the elongate, flexible portion further comprising a core and a sleeve surrounding the core and a plurality of electrically-conductive wires, each having a proximal end and a distal end coupled to at least one of the plurality of electrodes;
wherein the at least one polymer electrolyte member deforms asymmetrically in response to the application of an electrical potential supplied through at least one of the plurality of electrically-conductive wires to at least one of the plurality of electrodes, wherein the core comprises a tapered portion adjacent to the distal end of the elongate, flexible portion;
wherein the core extends inwardly to the polymer electrolyte member.

2. The medical device of claim 1, wherein the sleeve extends from the distal end of the elongate, flexible portion and surrounds at least a portion of the ionic electroactive polymer actuator.

3. The medical device of claim 2, wherein the electrically-conductive wires are secured between the sleeve and the core and are secured to at least a portion of the ionic electroactive polymer actuator.

4. The medical device of claim 1, wherein the polymer electrolyte member comprises an electrolyte and a polymer selected from the group consisting of fluoropolymers and intrinsically conducting polymers.

5. The medical device of claim 4, wherein the fluoropolymers are perfluorinated ionomers, polyvinylidene difluoride (PVDF) or co-polymer thereof.

6. The medical device of claim 4, wherein the intrinsically conducting polymers comprise polyaniline (PANI), polypyrrole (Ppy), poly(3,4-ethylenedioxythiophene) (PEDOT), poly(p-phenylene sulfide) (PPS) or the combination thereof.

7. The medical device of claim 1, wherein each of the electrodes comprises one of platinum, gold or a carbon-based material, or a combination of two or more of them.

8. The medical device of claim 7, wherein the carbon-based material comprises at least one of carbide-derived carbon, carbon nanotube, graphene, a composite of carbide-derived carbon and polymer electrolyte member, and a composite of carbon nanotube and polymer electrolyte member.

9. The medical device of claim 1, wherein the electrodes are circumferentially distributed about the at least one polymer electrolyte member with an equal angle therebetween.

10. The medical device of claim 1, wherein each of the electrically-conductive wires is disposed linearly along an exterior surface of the core.

11. The medical device of claim 1, wherein the elongate, flexible portion further comprises a plurality of grooves extending linearly, and spaced from each other circumferentially, along an exterior surface of the core, each groove receiving a one of the electrically-conductive wires.

12. The medical device of claim 1, wherein each of the plurality of electrically-conductive wires further comprise an insulation coating covered thereon.

13. The medical device of claim 1, further comprising a conductive bridge extending between a surface of the polymer electrolyte member and at least one of the electrodes.

14. The medical device of claim 1, wherein the core further comprises an inner lumen within which the electrically-conductive wires extend.

15. The medical device of claim 14, wherein the electrically-conductive wires further pass through the inner lumen.

16. The medical device of claim 1, wherein each of the plurality of electrically-conductive wires is helically or interweavingly wrapped around the core.

17. The medical device of claim 1, wherein the core comprises a metallic material to serve as an additional electrically-conductive conduit and couple to at least one of the plurality of electrodes.

18. The medical device of claim 1, wherein the ionic electroactive polymer actuator is configured to provide two degrees of freedom of movement thereof.

19. The medical device of claim 18, wherein four electrodes are circumferentially distributed form one another by equal angular degrees about the surface of the polymer electrolyte member.

20. The medical device of claim 1, wherein the ionic electroactive polymer actuator is configured to provide one degree of freedom of movement thereof.

21. The medical device of claim 20, wherein the polymer electrolyte member is in rodlike shape, and two electrodes are circumferentially distributed by equal angles about the surface of the polymer electrolyte member.

22. The medical device of claim 20, wherein the polymer electrolyte member is in rectangular shape and defines a top surface and a corresponding bottom surface and two electrodes are circumferentially distributed about the top surface and the bottom surface of the polymer electrolyte member symmetrically to form a sandwich structure.

23. The medical device of claim 22, wherein the core extends inwardly to a distal end of the polymer electrolyte member.

* * * * *